(12) United States Patent
Crump et al.

(10) Patent No.: US 9,968,400 B2
(45) Date of Patent: May 15, 2018

(54) ABLATION EMITTER ASSEMBLY

(71) Applicant: Perseon Corporation, Salt Lake City, UT (US)

(72) Inventors: Chet M. Crump, South Jordan, UT (US); Kent Moore, Bountiful, UT (US); Mark Sedlacek, Salt Lake City, UT (US); Todd H. Turnlund, Park City, UT (US)

(73) Assignee: PERSEON CORPORATION, Salt Lake City, UT (US)

( * ) Notice: Subject to any disclaimer, the term of this patent is extended or adjusted under 35 U.S.C. 154(b) by 87 days.

(21) Appl. No.: 14/310,951

(22) Filed: Jun. 20, 2014

(65) Prior Publication Data

US 2015/0366612 A1 Dec. 24, 2015

(51) Int. Cl.
*A61B 18/18* (2006.01)
*A61B 17/00* (2006.01)

(52) U.S. Cl.
CPC .. *A61B 18/1815* (2013.01); *A61B 2017/0088* (2013.01); *A61B 2018/1846* (2013.01); *A61B 2018/1869* (2013.01)

(58) Field of Classification Search
CPC .............. A61B 18/1815; A61B 18/18; A61B 2018/1846; A61B 2018/1869; A61B 2018/00577; A61B 2018/1892; A61B 2018/1861
See application file for complete search history.

(56) References Cited

U.S. PATENT DOCUMENTS

| | | | | |
|---|---|---|---|---|
| 4,161,950 A | * | 7/1979 | Doss .................. | A61B 18/1402 219/770 |
| 4,765,331 A | * | 8/1988 | Petruzzi ............. | A61B 18/1485 606/49 |
| 4,841,988 A | * | 6/1989 | Fetter ................. | A61B 18/1815 219/712 |
| 4,862,890 A | * | 9/1989 | Stasz .................. | A61B 18/1402 606/48 |
| 5,007,908 A | * | 4/1991 | Rydell ............... | A61B 18/1477 606/47 |
| 5,246,438 A | * | 9/1993 | Langberg ............... | A61B 18/08 600/374 |
| 5,470,352 A | * | 11/1995 | Rappaport ............. | A61B 18/18 606/194 |
| 5,620,480 A | * | 4/1997 | Rudie .................... | A61B 18/18 607/101 |
| 5,782,828 A | * | 7/1998 | Chen .................. | A61B 18/1206 604/95.01 |

(Continued)

*Primary Examiner* — Michael Peffley
(74) *Attorney, Agent, or Firm* — Dinsmore & Shohl LLP

(57) ABSTRACT

An emitter assembly can include a proximal shaft, a distal shaft, a shunt that connects the proximal shaft to the distal shaft, and a tip that is connected to a distal end of the distal shaft. An inner conductor can extend through the proximal shaft, the shunt, and the distal shaft and into the tip to provide microwave energy to the tip. An outer conductor can extend into the shunt. The shunt can therefore form an electrical connection between the outer conductor and a proximal ring of electrically conductive material formed on an exterior surface of the distal shaft. Distal shaft can be made of a thermally conductive but electrically insulated material to facilitate transfer of heat from the distal shaft to the proximal shaft.

23 Claims, 22 Drawing Sheets

(56) References Cited

U.S. PATENT DOCUMENTS

| | | | | |
|---|---|---|---|---|
| 5,810,803 A * | 9/1998 | Moss | ................ | A61B 18/1492 606/33 |
| 5,974,343 A * | 10/1999 | Brevard | ................ | A61B 18/18 607/102 |
| 6,325,800 B1 * | 12/2001 | Durgin | ............... | A61B 18/1492 606/41 |
| 6,878,147 B2 * | 4/2005 | Prakash | ................ | A61B 18/18 606/33 |
| 8,934,989 B2 * | 1/2015 | Ormsby | ................ | A61B 18/18 606/41 |
| 2011/0213352 A1 * | 9/2011 | Lee | .................... | A61B 18/1815 606/33 |

* cited by examiner

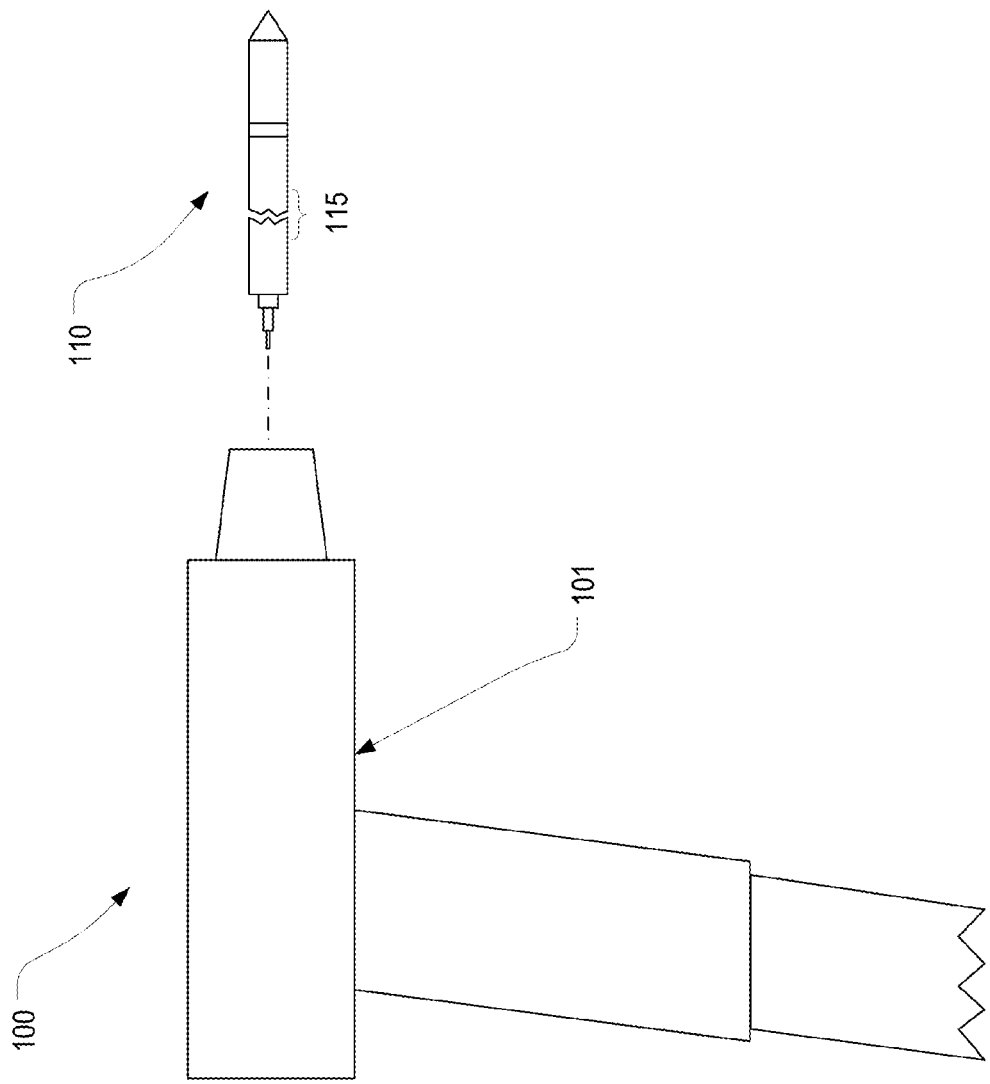

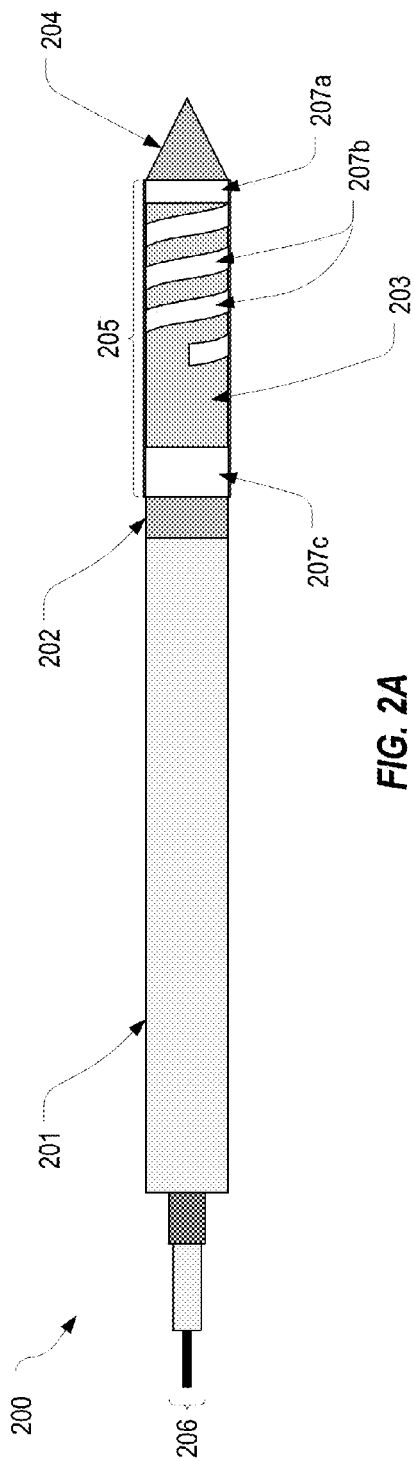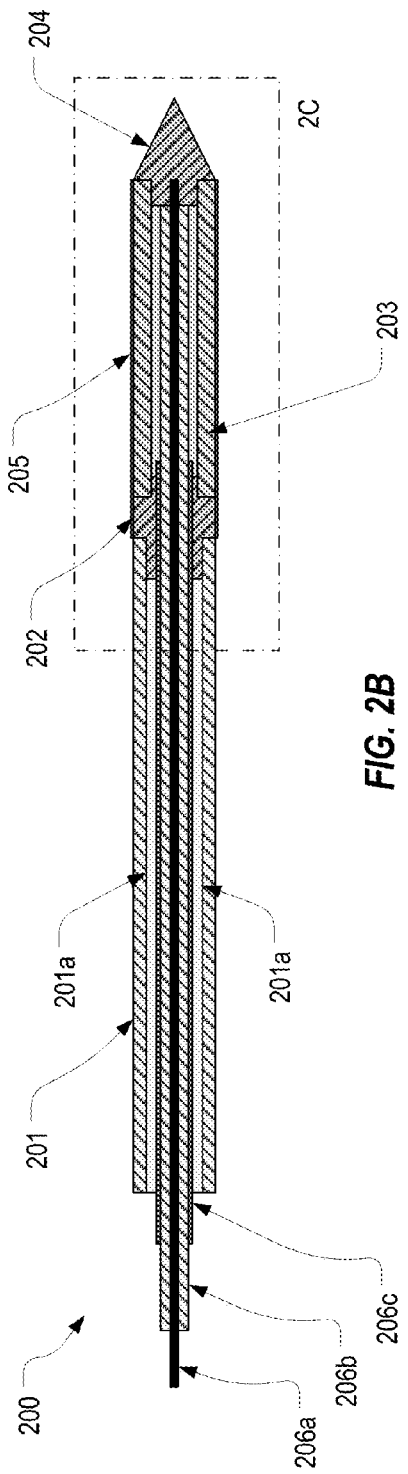
FIG. 2A
FIG. 2B

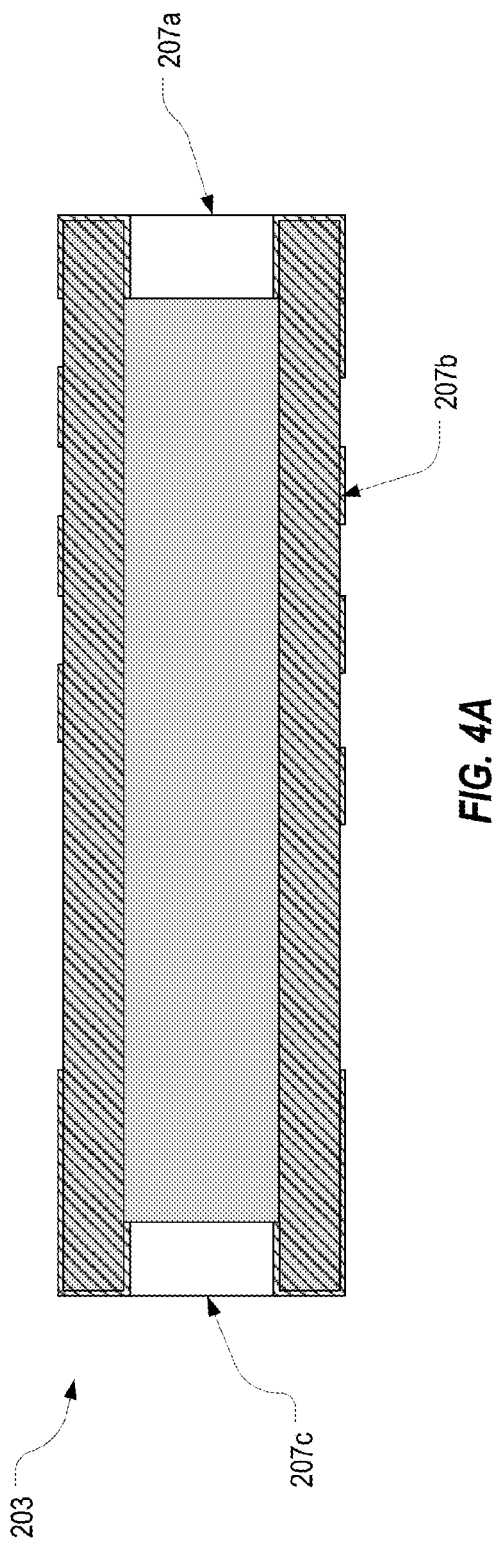
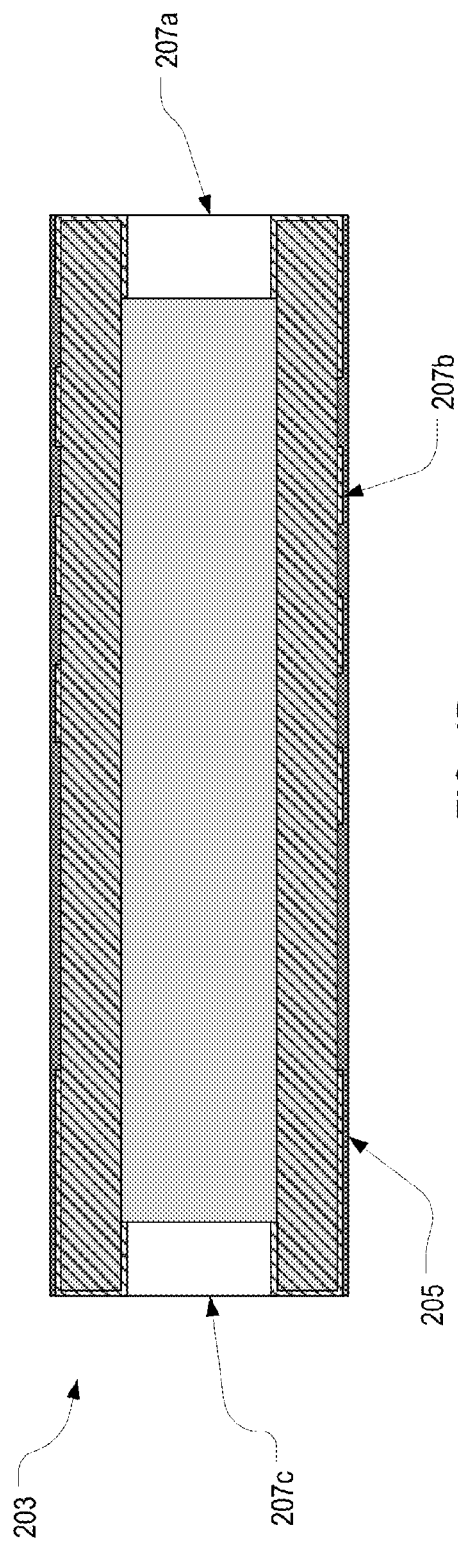
FIG. 4A
FIG. 4B

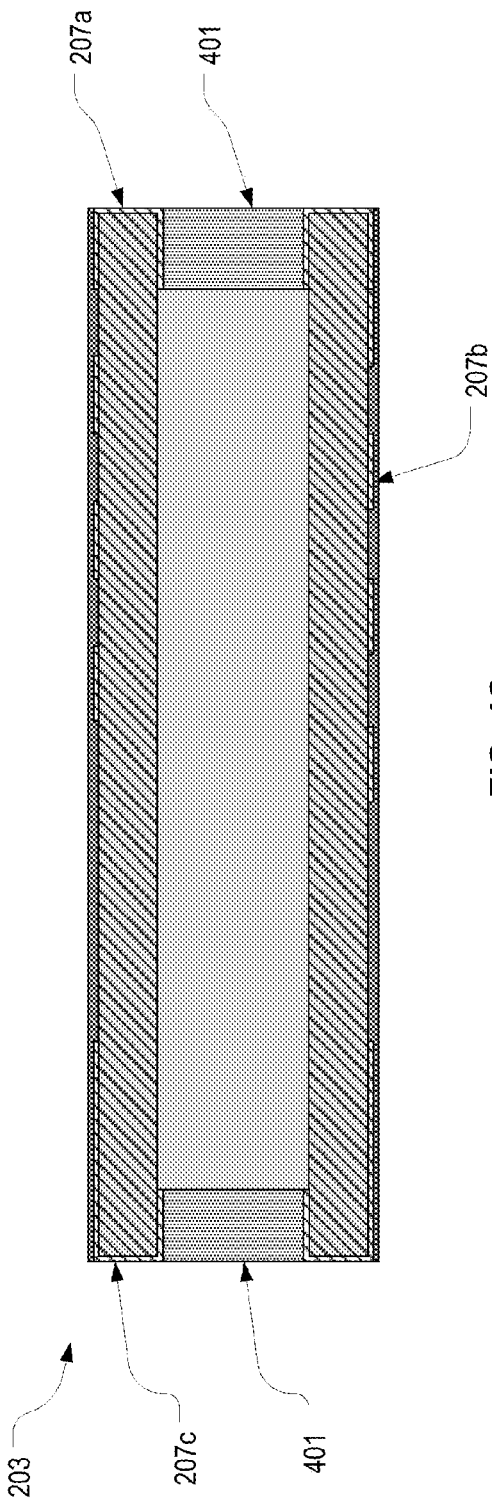
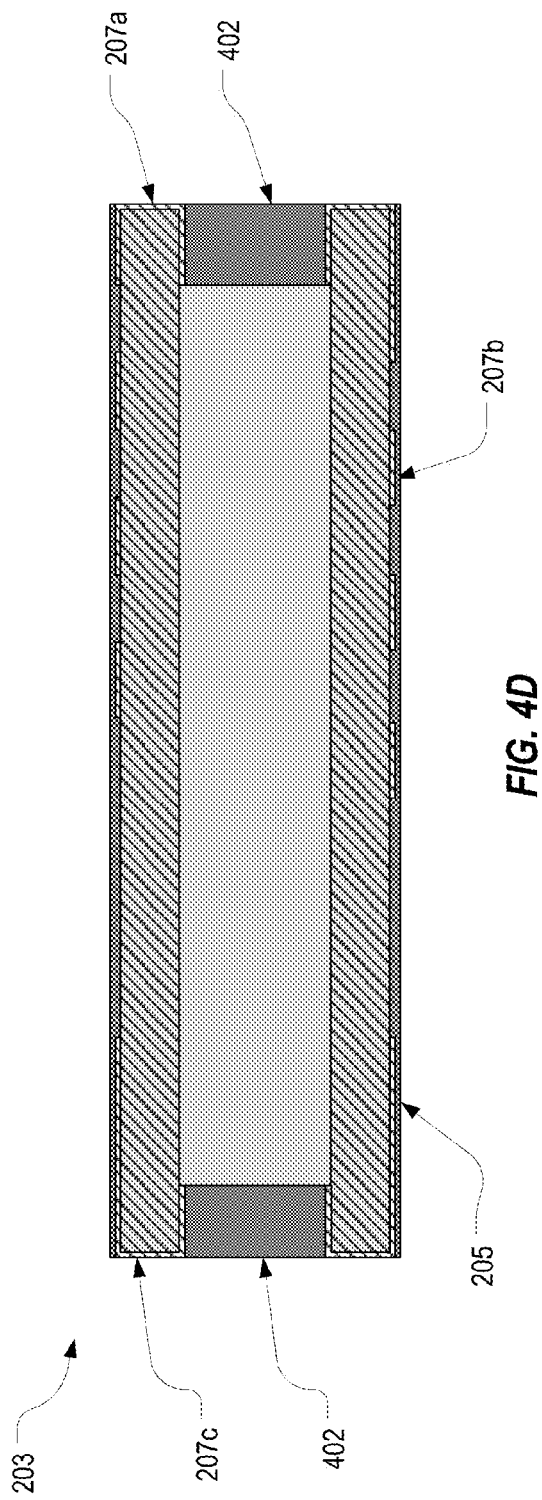

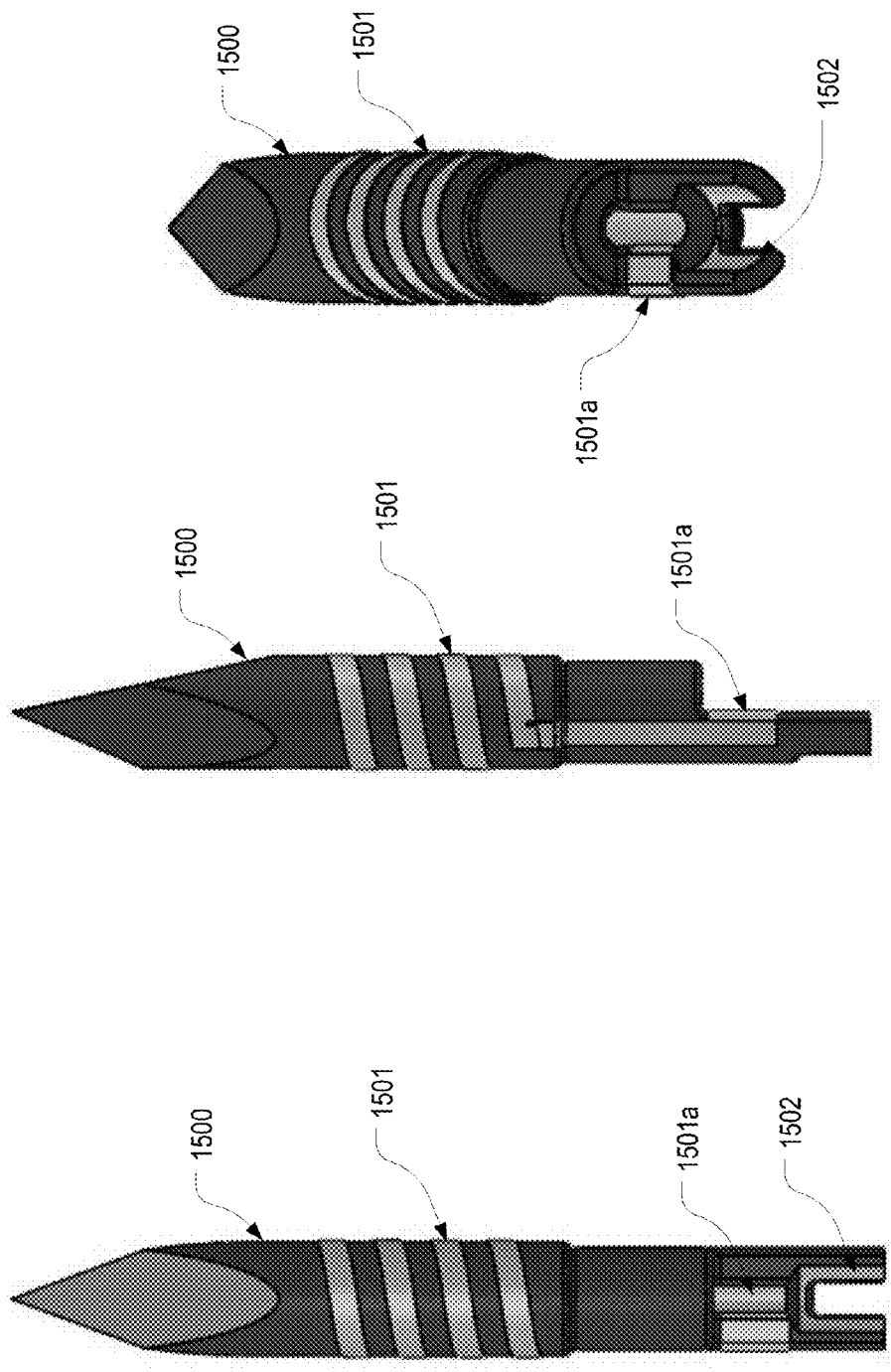

ABLATION EMITTER ASSEMBLY

CROSS-REFERENCE TO RELATED APPLICATIONS

N/A

BACKGROUND

Microwave ablation (MWA) is a medical procedure where in vivo tissue is ablated using high frequency electromagnetic field to treat a medical disorder. MWA is commonly performed to treat tumors in body organs. During MWA, a needle-like MWA probe is placed inside the tumor. Microwaves emitted from the probe heat surrounding tumor tissue, destroying the target tissues, such as soft tissue, cancerous tumor, nerve, or other target structure. Cancer cells, in particular, break down and die at elevated temperatures caused by MWA procedures. Some MWA procedures create temperatures up to or exceeding 300 degrees Celsius.

For MWA to be successful, a sufficient amount of molecular agitation must occur within the tissue. For example, the varying electromagnetic field generated by the waves emitted from the MWA probe causes water molecules to rapidly vibrate as they attempt to align with the varying field. This molecular agitation creates frictional heat which is capable of rapidly increasing the temperature of the tissue in a similar manner as a microwave oven heats food.

It is desirable to heat the entire area of the tumor with a single treatment. However, it is difficult to obtain even heat distribution using current ablation techniques. When heated to above 60° C., tissue will immediately coagulate.

BRIEF SUMMARY

The present invention extends to an emitter assembly that can be used to perform microwave ablation (MWA). The design of the emitter assembly can facilitate transfer of microwave energy into a patient's tissue while also facilitating transfer of internal heat towards a proximal end of the emitter assembly thereby enabling operation of the emitter assembly at higher power without sacrificing the accuracy of the ablation pattern.

In one embodiment, the present invention is implemented as an emitter assembly for performing an ablation that includes a proximal shaft, a distal shaft having an exterior surface, a tip that extends from a distal end of the distal shaft, an inner conductor that extends through the proximal shaft, an outer conductor, and a conductive trace formed on the exterior surface of the distal shaft.

The distal shaft may be comprised primarily of ceramic including alumina based ceramic or zirconia based ceramic. The tip may be the same component as or a separate component from the distal shaft. The tip may also be comprised of an inner and an outer component. The conductive trace may spiral around the exterior surface. The conductive trace may be metallized onto the exterior surface of the distal shaft. The conductive trace may extend in a proximal or a distal direction. The conductive trace may also comprise multiple conductive traces that extend in a proximal and a distal direction.

The distal shaft may include a distal ring and/or a proximal ring that is formed on one or both of an interior surface or an exterior surface of the distal shaft. The tip may form an electrical connection between the inner conductor and the distal ring. The conductive trace may be electrically connected to the distal ring and/or the proximal ring.

The emitter assembly may include a shunt that connects the proximal shaft to the distal shaft. The shunt may form an electrical connection with the outer conductor. The proximal ring may be electrically connected to the shunt.

The emitter assembly may include an insulator positioned between the inner and outer conductors. The insulator may comprise PTFE or ceramic. The inner assembly may include an outer coating that covers at least a portion of an exterior surface of the distal shaft. The outer coating may cover one or more of the tip, the shunt, or the proximal shaft. The outer coating may comprise one or more layers or may comprise glass, PTFE, or diamond-like carbon. The emitter assembly may comprise one or more inner coatings applied on an inner surface of the distal shaft. The one or more inner coatings may be applied over a portion of the proximal and/or distal rings that extends along an inner surface of the distal shaft.

In another embodiment, the present invention is implemented as an emitter assembly for performing an ablation that includes a distal shaft, a tip that extends from a distal end of the distal shaft, a trace that extends along an exterior surface of the distal shaft, and an outer coating applied on the exterior surface overtop the trace. The distal shaft may be comprised of ceramic.

In another embodiment, the present invention is implemented as an emitter assembly for performing an ablation that includes a proximal shaft, a distal shaft, and a shunt for connecting the proximal shaft to the distal shaft. The shunt comprises a conductive material for transferring heat from the distal shaft to the proximal shaft.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 illustrates a microwave ablation device that can be used in MWA ablation procedures;

FIG. 2A illustrates a front view of an example emitter assembly in accordance with one or more embodiments of the invention;

FIG. 2B illustrates a cross-sectional view of the emitter assembly of FIG. 2A;

FIG. 4A illustrates a cross-sectional view of a distal shaft after the distal ring, the trace, and the proximal ring have been applied;

FIG. 4B illustrates a cross-sectional view of the distal shaft of FIG. 4A after an outer coating has been applied;

FIG. 4C illustrates a cross-sectional view of the distal shaft of FIG. 4B after a first inner coating has been applied;

FIG. 4D illustrates a cross-sectional view of the distal shaft of FIG. 4C after a second inner coating has been applied;

FIGS. 15A-15C illustrate different views of a tip that can be used in place of the distal shaft and tip shown in FIG. 2A.

DETAILED DESCRIPTION

Figure 2C:
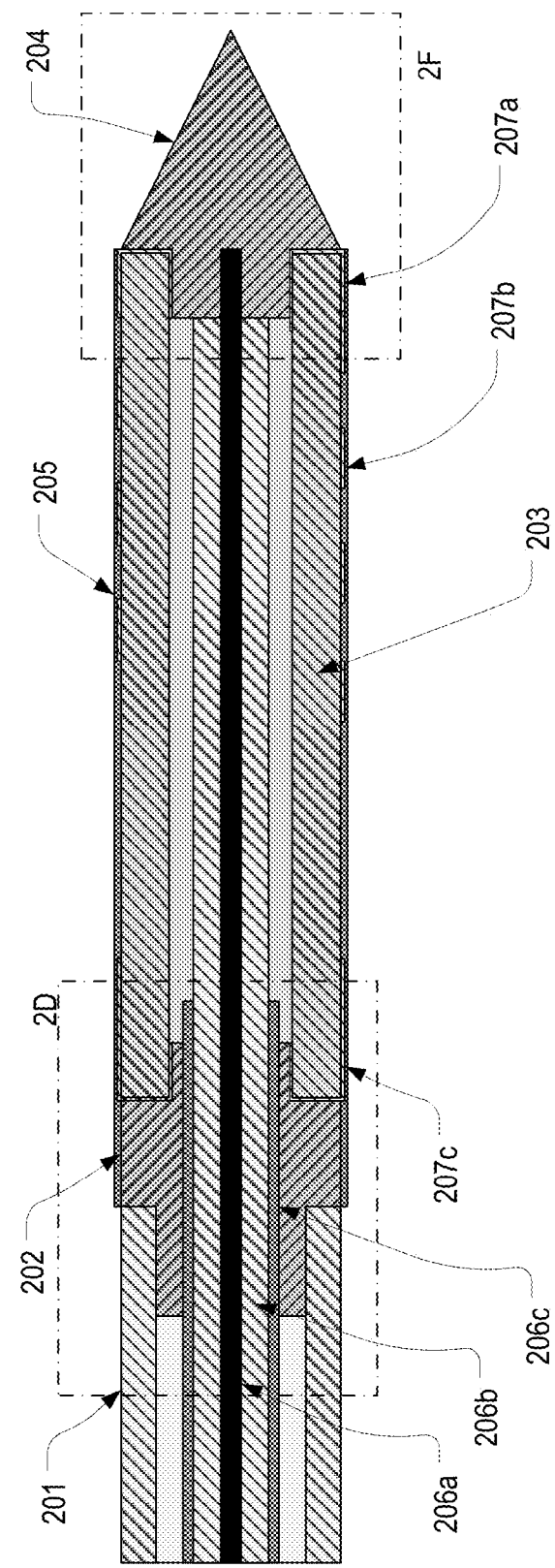
FIG. 2C illustrates a detailed view of a distal portion of FIG. 2A.

FIG. 1 is intended to provide an overview of the general architecture of a microwave ablation (MWA) device 100 that can be used in MWA procedures. The MWA device 100 can include a body 101 and an emitter assembly 110 that is configured to attach to and extend from a distal end of body 101. Emitter assembly 110 can have various lengths as indicated by the break 115 in FIG. 1 and may typically be between 1 and 12 inches. The gauge of emitter assembly 110 can range between 8 to 24, including, but not limited to, an 11, 13, 14, 16, 17, or 18 gauge.

Body 101 typically includes (or provides access to) a microwave power source (not shown) for supplying microwave energy to emitter assembly 110. Emitter assembly 110 comprises an antenna for emitting the microwave energy into surrounding tissue when emitter assembly 110 is inserted within a patient's tissue.

Body 101 may also include (or provide access to) a controller (not shown) for controlling the power, frequency, and/or phase of the microwave energy delivered to emitter assembly 110. In some embodiments, the controller can be configured to automatically adjust the power, frequency, and/or phase of the microwave energy delivered to emitter assembly 110 in order to tune or impedance match the emitter assembly to surrounding tissue.

The MWA device 100 can be configured to transmit energy having one or more frequencies or a variable frequency. For example, in some embodiments, the microwave power source is a microwave source configured to provide microwave energy to emitter assembly 110. Such energy can have a frequency within the range of about 300 MHz to 30 GHz. In some embodiments, a specific frequency of 915 or 2,450 MHz may be preferred. When microwave energy is delivered to emitter assembly 110, tissue surrounding emitter assembly 110 can be ablated by heat generated by emitter assembly 110.

Additionally, the microwave power source can be configured to transmit various levels of energy to emitter assembly 110. In some embodiments, the microwave power source can transmit up to about 300 W of power to emitter assembly 110. In other embodiments, the microwave power source can transmit between 0 W to 300 W of power to emitter assembly 110, including specifically transmitting up to 40 W, up to 60 W, up to 120 W, up to 180 W, or up to 240 W of power to emitter assembly 110.

In some embodiments, the controller can be configured to ramp up the power delivered to emitter assembly 110 slowly during the initial phases of an ablation procedure. Such configurations can incrementally, exponentially, or otherwise ramp up power from zero to a maximum power output over a predetermined time. For instance, the controller can be configured to ramp up power delivered to emitter assembly 110 from 0 W to 60 W over a time period.

During MWA, emitter assembly 110 is inserted through the skin and tissue of a patient, and is then directed toward a target structure, such as a tumor, cell(s), or nerve(s). Emitter assembly 110 can be inserted into the target structure or placed beside the target structure. Microwave energy emitted from emitter assembly 110 can then heat the target structure, which may be ablated and/or killed. When the target structure is exposed to the transmitted microwave energy for an adequate amount of time and temperature, the target structure can be ablated. Cancer cells, in particular, can break down and die at elevated temperatures caused by MW ablation procedures. Some MWA procedures create temperatures up to or exceeding 100 to 350 degrees Celsius.

Generally, the shape and size of an ablation pattern produced by emitter assembly 110 roughly corresponds to the shape and intensity of the microwave transmission patterns of the waves emitted from emitter assembly 110. Thus, a substantially spherical transmission pattern can produce a roughly spherical ablation pattern. Accordingly, emitter assembly 110 can be configured to produce ablation regions that are substantially the same size as the target structure so that the appropriate amount of target tissue is ablated, without ablating healthy surrounding tissues. For example, since many tumors are approximately spherical, emitter assembly 110 can be configured to produce a generally spherical ablation region.

Additionally, emitter assembly 110 can be configured to produce ablation regions that are directional and dose-able (or shapeable) so that they can be shaped to be the same size as a target structure or so that they can be directed toward a target structure near emitter assembly 110. Such directionality can be produced, in some instances, by varying the phase between transmitted microwave energy transmitted through multiple conductors of emitter assembly 110.

FIG. 2A illustrates an example configuration of an emitter assembly 200 in accordance with one or more embodiments of the invention. Emitter assembly 200 can be used with body 101 as described above, or with any other type of suitable body that can supply microwave energy to emitter assembly 200.

Figure 3:
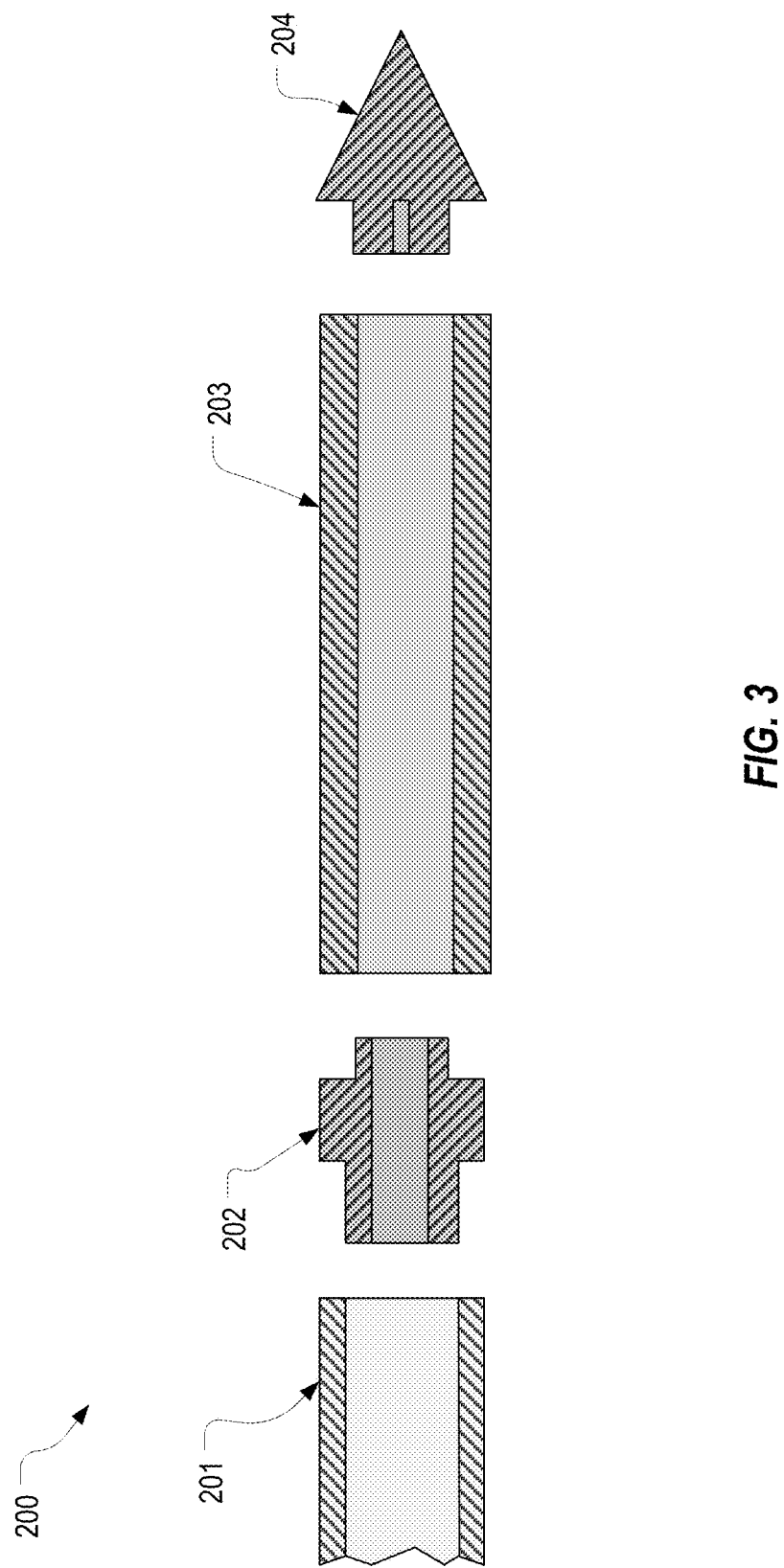
FIG. 3 illustrates an exploded view of some of the components of the emitter assembly depicted in FIG. 2B.

Emitter assembly 200 comprises a proximal shaft 201, a distal shaft 203, a shunt 202 positioned between and connecting proximal shaft 201 and distal shaft 203, and a tip 204 positioned at a distal end of distal shaft 203. An exploded view of these four components of emitter assembly 200 is shown in FIG. 3.

Emitter assembly 200 also includes a conductor 206 that extends through emitter assembly 200. Conductor 206 is configured to connect to a source of microwave energy (e.g. via body 101) and transmit the microwave energy to tip 204 as will be further described below.

Distal shaft 203 includes a distal ring 207a that extends around distal shaft 203 and is positioned adjacent tip 204. Distal shaft 203 also includes a trace 207b that extends from distal ring 207a and wraps around distal shaft 203 in a helical pattern. Distal shaft 203 further includes a proximal ring 207c that extends around distal shaft 203 and is positioned adjacent shunt 202. The connections between conductor 206 and distal ring 207a, trace 207b, and proximal ring 207c will be further described below with reference to FIG. 2B. Although distal ring 207a and proximal ring 207c are shown as extending completely around distal shaft 203, distal ring 207a and proximal ring 207c may equally extend only partially around distal shaft 203. As is further described below, the distal and proximal rings are comprised of a conductive material and can serve to interconnect one or more traces with another component of an emitter assembly.

Although not shown, proximal shaft 201 can contain and circulate a cooling fluid (e.g. saline) for cooling emitter assembly 200, and in particular, for removing heat from shunt 202 and proximal shaft 201. Further, emitter assembly 200 may also include one or more outer coatings 205. In FIG. 2A, outer coating(s) 205 is identified as being applied only from shunt 202 and distal shaft 203 (e.g. to cover distal ring 207a, trace 207b, and proximal ring 207c. However, in some embodiments, outer coating(s) 205 may also extend overtop tip 204 and/or proximal shaft 201. In other words, outer coating(s) 205 may cover a portion of or the entire outer surface of emitter assembly 200. In some embodiments, outer coating(s) 205 may only be applied overtop distal shaft 203 so as to cover and protect distal ring 207a, trace 207b, and proximal ring 207c as will be further described below.

Figure 2D:
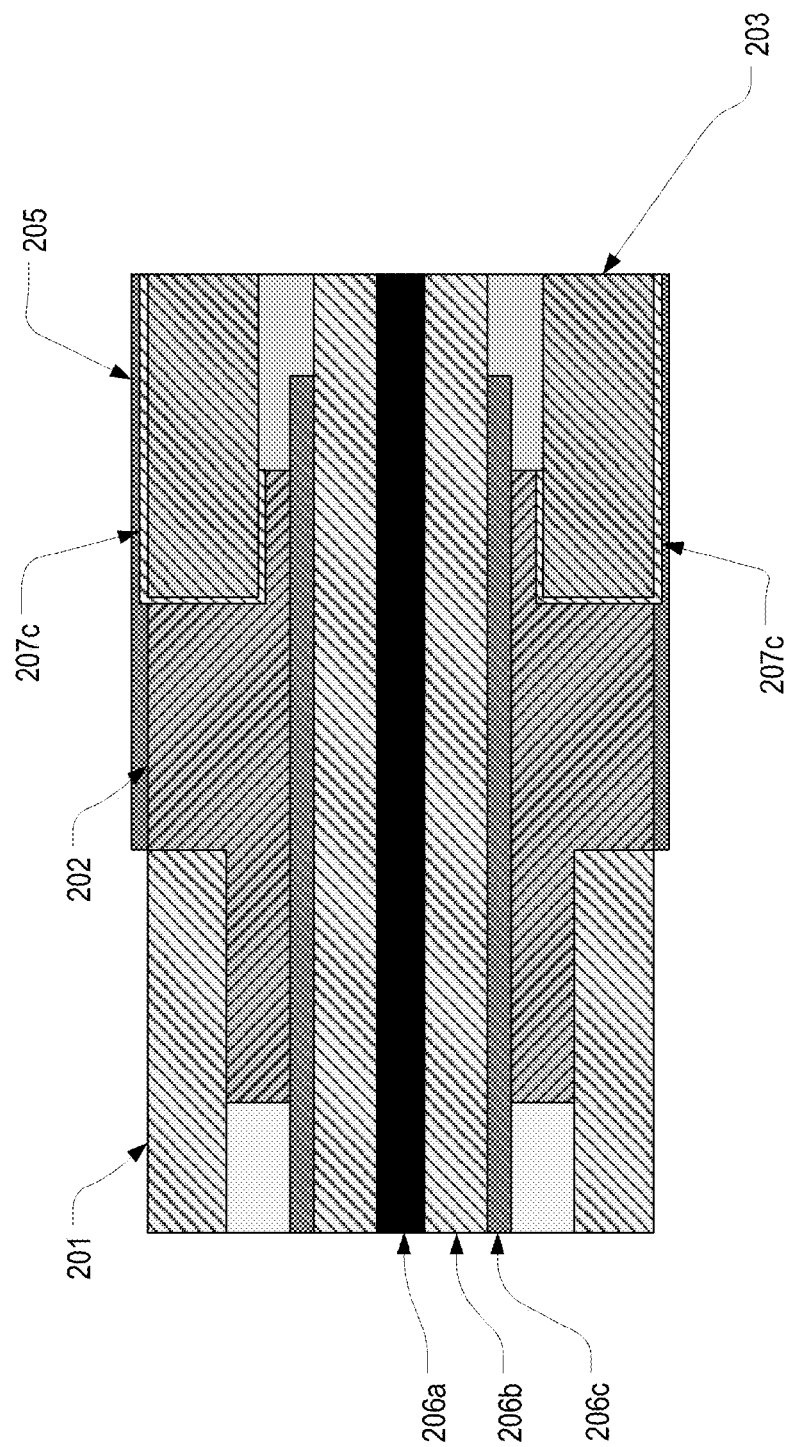
FIG. 2D illustrates a detailed view of the shunt depicted in FIG. 2C.
Figure 2E:
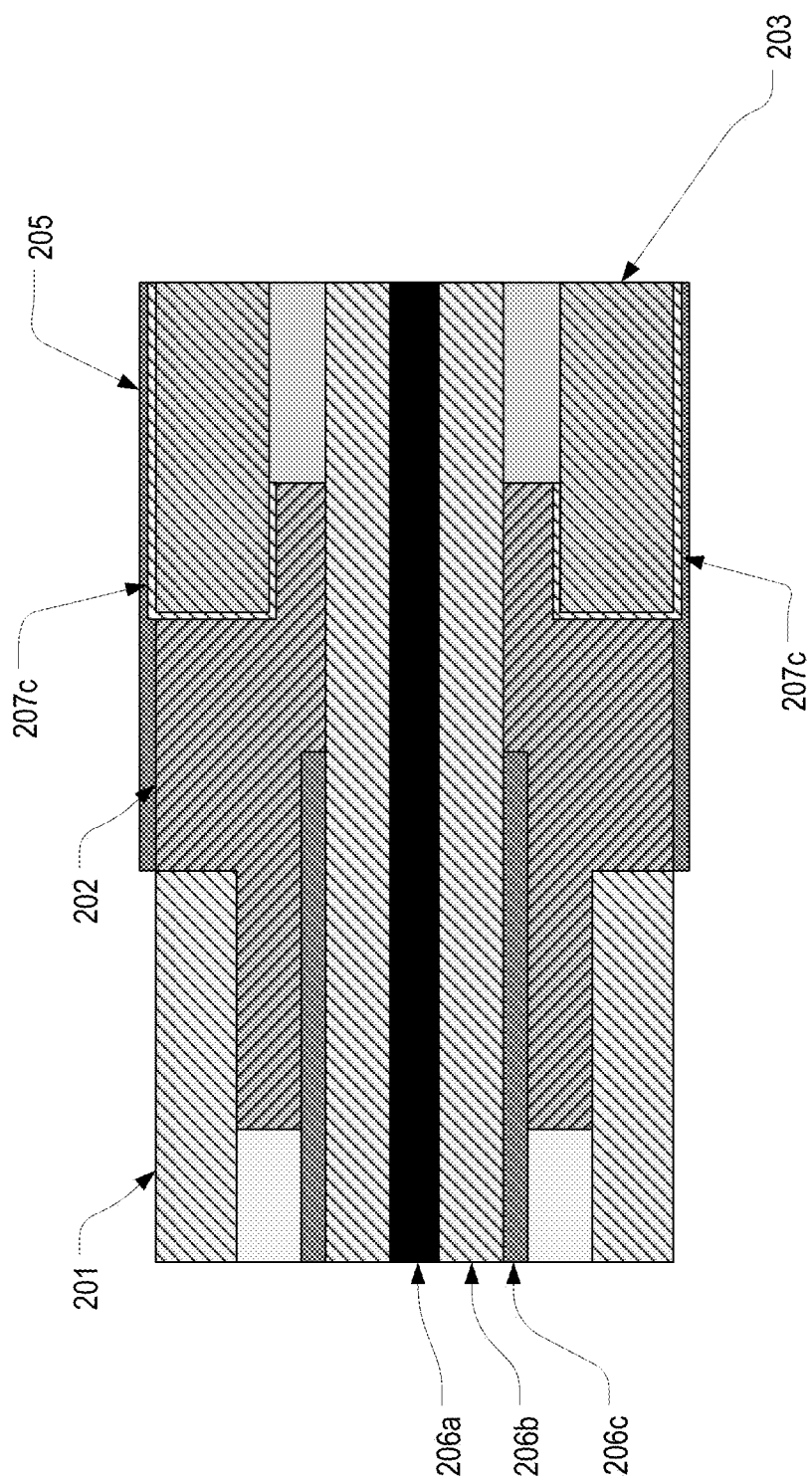
FIG. 2E illustrates a detailed view of an alternate implementation of the shunt depicted in FIG. 2D.
Figure 2F:
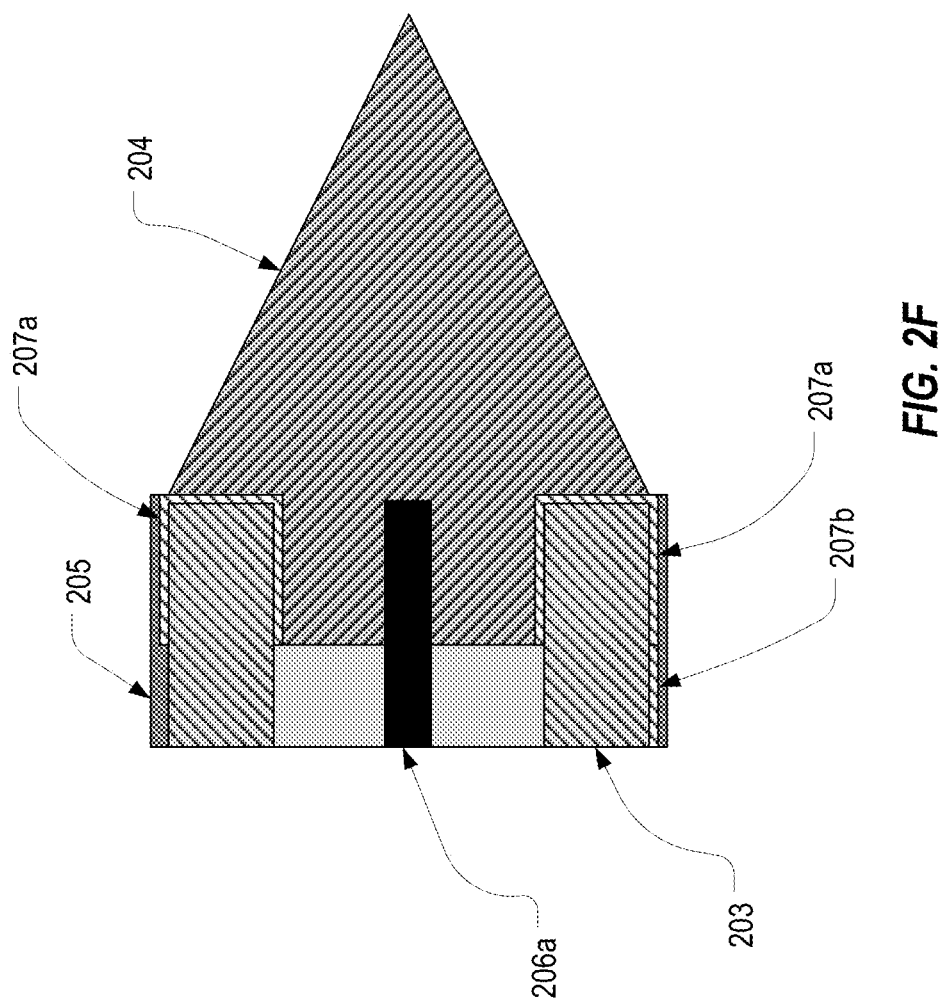
FIG. 2F illustrates a detailed view of the tip depicted in FIG. 2C.

FIG. 2B provides a cross-sectional view of emitter assembly 200 while FIGS. 2C, 2D, and 2F each provide a detailed view of a portion of the cross-sectional view of FIG. 2B. FIG. 2E provides a cross-sectional view of an alternate configuration of shunt 202 in which outer conductor 206c extends only partially into shunt 202.

As shown, shunt 202 is shaped and sized so as to fit within a distal end of proximal shaft 201 and within a proximal end of distal shaft 203. Similarly, tip 204 is shaped and sized so as to fit within a distal end of distal shaft 203. Both shunt 202 and tip 204 are formed of an electrically and possibly thermally conductive material (e.g. brass, stainless steel, titanium, etc.) that may be suitable for connection via soldering, brazing or other appropriate means.

Conductor 206 is comprised of a center conductor 206a, an insulator 206b, and an outer conductor 206c. Center conductor 206a extends distally into tip 204 and therefore forms an electrical connection with tip 204. Accordingly, microwave energy may be transmitted by center conductor 206a into tip 204. Outer conductor 206c extends into (if not through as shown in FIG. 2B) shunt 202 and therefore forms an electrical connection with shunt 202. In some embodiments, proximal shaft 201 can be made of a conductive material and will therefore form an electrical connection with shunt 202 and outer conductor 206c. Insulator 206b extends up to tip 204 to insulate and isolate center conductor 206a from the other components of emitter assembly 200. In other embodiments, proximal shaft 201 can be made of a non-conductive, low loss dielectric insulator with a low dielectric constant. Suitable insulators include PVC, fiberglass, PEEK, and nylon, among others.

As also shown in FIG. 2B, a void 201a is formed within proximal shaft 201 between the inner wall of proximal shaft 201 and conductor 206. The cooling fluid mentioned above can circulate within void 201a to remove heat from the distal end of emitter assembly 200 (e.g. via shunt 202).

As best shown in FIGS. 2D and 2E, proximal ring 207c forms a coating not only on the outer surface of distal shaft 203, but also on the distal end and the inner surface of distal shaft 203. In some embodiments, including as shown in FIGS. 2D and 2E, proximal ring 207c can extend within distal shaft 203 to a depth that is approximately the same as the depth to which shunt 202 inserts into distal shaft 203. In this manner, proximal ring 207c forms a conductive extension of shunt 202 (and therefore outer conductor 206c) that extends distally along the outer surface of distal shaft 203. In typical implementations, outer conductor 206c functions as a ground, and therefore, in such implementations, proximal ring 207c functions as a ground plane.

As best shown in FIG. 2F, distal ring 207a can be configured similar to proximal ring 207c in that it also extends around the distal end of distal shaft 203 and onto the inner surface of distal shaft 203. In some embodiments, including as shown in FIG. 2F, distal ring 207a can extend within distal shaft 203 to a depth that is approximately the same as the depth to which tip 204 inserts into distal shaft 203. In this manner, distal ring 207a forms a conductive extension of tip 204 (and therefore center conductor 206a).

As is also best shown in FIG. 2F, a distal end of trace 207b is connected to distal ring 207a. Trace 207b is therefore electrically connected with inner conductor 206a thereby allowing trace 207b to function as an antenna for the microwave energy transmitted via center conductor 206a.

Figure 2G:
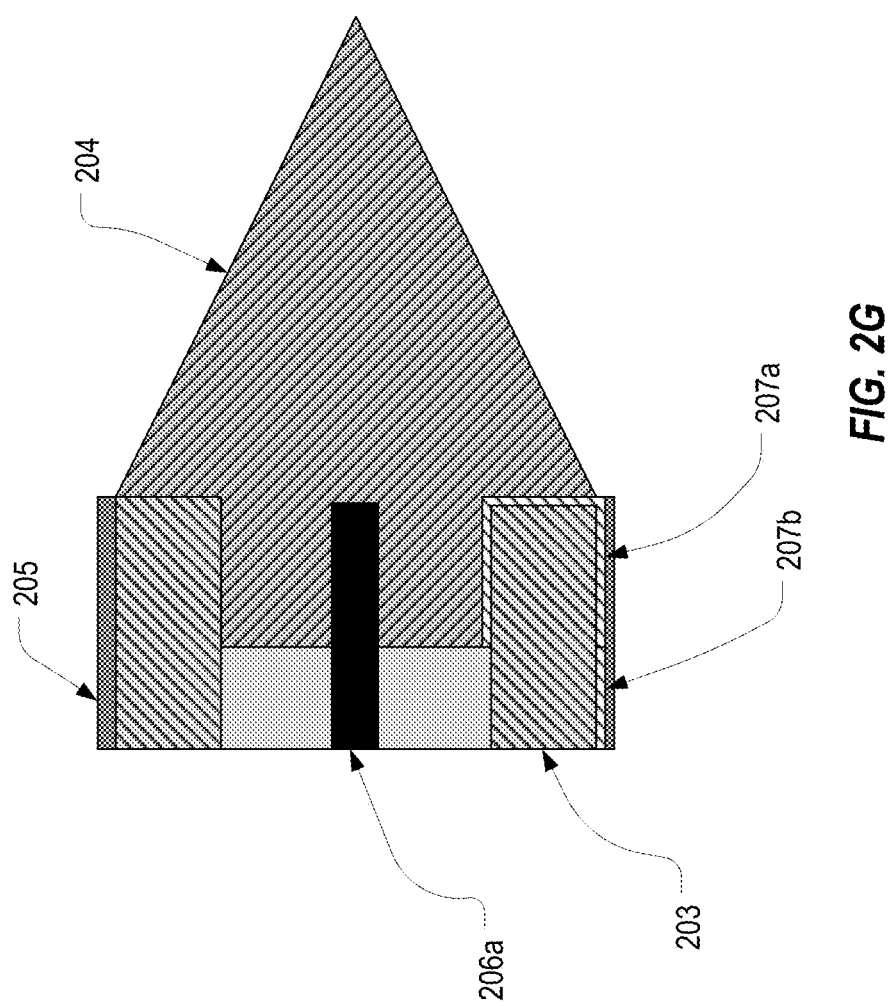
FIG. 2G illustrates a detailed view of an alternate implementation of the tip depicted in FIG. 2F.

As stated above, distal ring 207a and/or proximal ring 207c need not extend completely around distal shaft 203. FIG. 2G illustrates an example where distal ring 207a extends only partially around distal shaft 203. As shown, distal ring 207a is not present at the top of distal shaft 203. In some embodiments, distal ring 207a and/or proximal ring 207c may extend around different amounts of the inner and outer surfaces of distal shaft 203. For example, distal ring 207a may extend completely around the inner surface of distal shaft 203 but only extend 180 degrees around the exterior surface. Similarly, distal ring 207a may extend 180 degrees around the inner surface of distal shaft 203 while only including a small portion (e.g. similar to the width of trace 207b) that extends around the outer surface. In such cases, it may be accurate to say that no part of distal ring 207a extends around the exterior surface, but trace 207b extends up to and connects with a portion of distal ring 207a that is formed on an inner surface.

FIGS. 4A-4D illustrate cross-sectional views of distal shaft 203 in isolation. FIG. 4A illustrates distal shaft 203 with distal ring 207a, trace 207b, and proximal ring 207c. FIG. 4B illustrates that outer coating(s) 205 has been applied on distal shaft 203 overtop distal ring 207a, trace 207b, and proximal ring 207c. As stated above, outer coating(s) 205, in some embodiments, may only be applied over distal shaft 203 as shown in FIG. 4B while in other embodiments may be applied over one or more of tip 204, shunt 202, or proximal shaft 201.

In some embodiments, additional inner coatings may be applied to the proximal and/or distal ends of distal shaft 203. For example, as shown in FIG. 4C, a first inner coating 401 may be applied within the proximal and distal ends of distal shaft 203 overtop proximal ring 207c and distal ring 207a. In some embodiments, a second inner coating 402 may also be applied overtop of first inner coating 401 as shown in FIG. 4D. First and/or second inner coatings 401/402 can be applied to enhance the connection and/or increase the conductivity between proximal ring 207c and shunt 202 and between distal ring 207a and tip 204. In other words, the connection between proximal ring 207c and shunt 202 can be increased by including one or both of inner coatings 401/402 as intermediate layers. Similarly, the connection between distal ring 207a and tip 204 can be increased by including one or both of inner coatings 401/402 as intermediate layers.

In some embodiments of the present invention, distal shaft 203 can be formed of ceramic. For example, distal shaft 203 can be formed from aluminum oxide, aluminum nitride, zirconia toughened alumina, zirconia, partially stabilized zirconia, silicon carbide, or other ceramic material. Ceramic can be preferred in some embodiments because it is an electrical insulator that is also strong and tolerant of high temperatures with low to moderate thermal conductivity. Accordingly, a distal shaft formed of a ceramic can provide high electrical insulation between trace 207b and proximal ring 207c while also providing thermal conductance to allow heat to be transferred efficiently from tip 204 to shunt 202 where it can be dissipated via the cooling fluid within proximal shaft 201. This cooling of emitter assembly 200 can assist in enabling emitter assembly 200 to obtain spherical ablations.

In embodiments where distal shaft 203 is formed of ceramic, distal ring 207a, trace 207b, and proximal ring 207c can be formed of a metal conductor such as silver, copper, gold, aluminum, nickel, molybdenum ("moly") manganese, brass, or other conductor. In particular, the ceramic distal shaft can be metallized to form distal ring 207a, trace 207b, and proximal ring 207c with tight bonding to distal shaft 203. This tight bonding can be formed by heating the metal to high temperatures while on the ceramic so that the metal adheres to the ceramic. Metallizing ceramic refers to the process of applying one or more layers of metal on the surface of the ceramic and then heating the ceramic to cause the metal to bond with the ceramic. Various techniques exist for metallizing ceramic that would be suitable for metallizing a component of an emitter assembly. For example, a thick film ink containing a moly manganese refractory formula or another metal can be applied through a screen, roll printing, hand painting, air brush spraying, immersion, centrifugal coating, needle painting, etc. to a ceramic component and fired at temperatures sufficient to cause bonding of the metal to the ceramic.

Outer coating(s) 205 can be employed to cover distal ring 207a, trace 207b, and proximal ring 207c for various reasons including to isolate them from a patient's tissue, to protect them from decomposition (e.g. via oxidation), and to provide a smooth surface. In some embodiments, outer coating(s) 205 can be comprised of glass or ceramic which may be preferred due to its high dielectric value which helps microwaves emitted from trace 207b transition into surrounding tissue.

In some embodiments, a material that provides a non-stick surface may be preferred and multiple coatings may be used for outer coating(s) 205. For example, outer coating(s) 205 can be formed of glass or Polytetrafluoroethylene (PTFE) to prevent ablated tissue from sticking to the outer surface of emitter assembly 200 (e.g. to the outer surface of tip 204, distal shaft 203, shunt 202, and/or proximal shaft 201). In some embodiments, a glass outer coating(s) 205 can be employed with an additional PTFE coating overtop the glass. In this way, the benefits of a glass coating can be obtained while also having a non-stick PTFE or diamond-like carbon surface.

In some embodiments, tip 204 may also be formed of a ceramic. In such cases, a conductive coating (e.g. a copper, silver, nickel, gold or moly manganese coating) can be applied to the inner surfaces of tip 204 to form an electrical connection between distal ring 207a and center conductor 206a. Forming tip 204 of ceramic can be preferred in embodiments where it is desirable that the visibility of tip 204 via x-ray be minimized. In other embodiments, tip 204 can be formed of brass, titanium, or low thermo-expansion metals.

In some embodiments of the invention, insulator 206b may be formed of PTFE. In other embodiments, however, insulator 206b may be formed of a ceramic such as an aluminum oxide based ceramic to enhance the dissipation of heat from within center conductor 206a. A ceramic insulator 206b would also be able to withstand higher temperatures than Teflon. For example, Teflon can melt when center conductor 206a heats it to above 300° C. which can occur during high power transmission. By using a ceramic insulator 206b, emitter assembly 200 could be operated at higher wattages without the risk of melting insulator 206b. This ability to operate at higher temperatures and wattages would enable emitter assembly 200 to be used to perform larger diameter ablations.

In some embodiments, first inner coating 401 can be comprised of moly manganese while second inner coating 402 can be comprised of nickel. In some embodiments, a third inner coating may also be employed and may be comprised of gold, copper, silver, or another metal. Employing second inner coating 402 (and in some cases, a third inner coating) can be preferred because it enables tip 204 and shunt 202 to be secured to distal shaft 203 by soldering or brazing. In some embodiments, proximal shaft 201 can be formed of stainless steel. In some embodiments, outer conductor 206c can be formed of solder filler although any conductive material can be used. In some embodiments, a dielectric material may be disposed within the void (not labeled) between the inner surface of distal shaft 203 and insulator 206b. For example, a PTFE, polyimide (e.g. Kapton®), silicone, a high temperature resistant polymer, or a ceramic material could be used. In some embodiments, insulator 206b can be configured with a sufficient diameter so that there is little or no void.

Figure 5A:
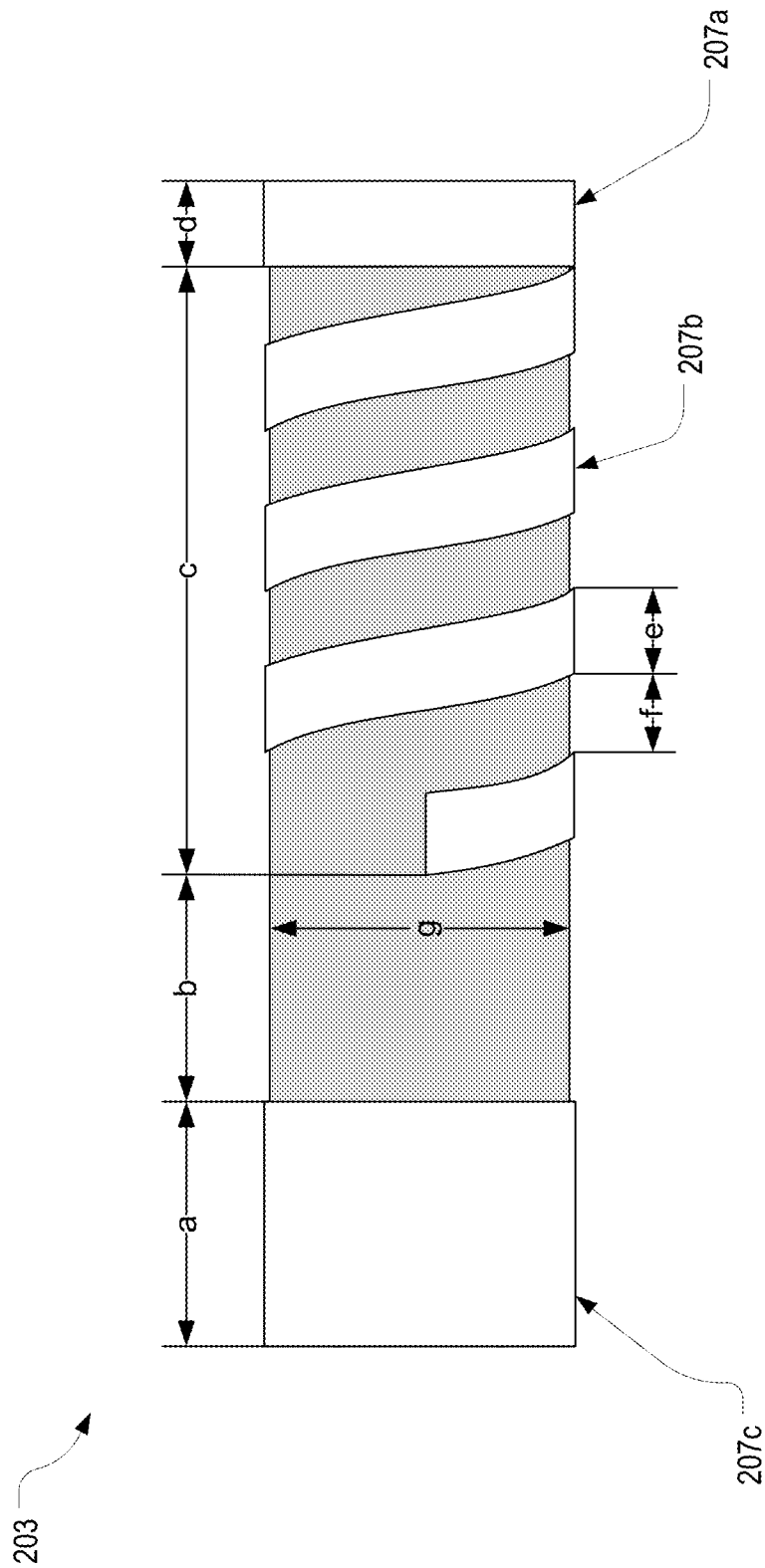
FIG. 5A illustrates a front view of a distal shaft with various dimensions labeled.
Figure 5B:
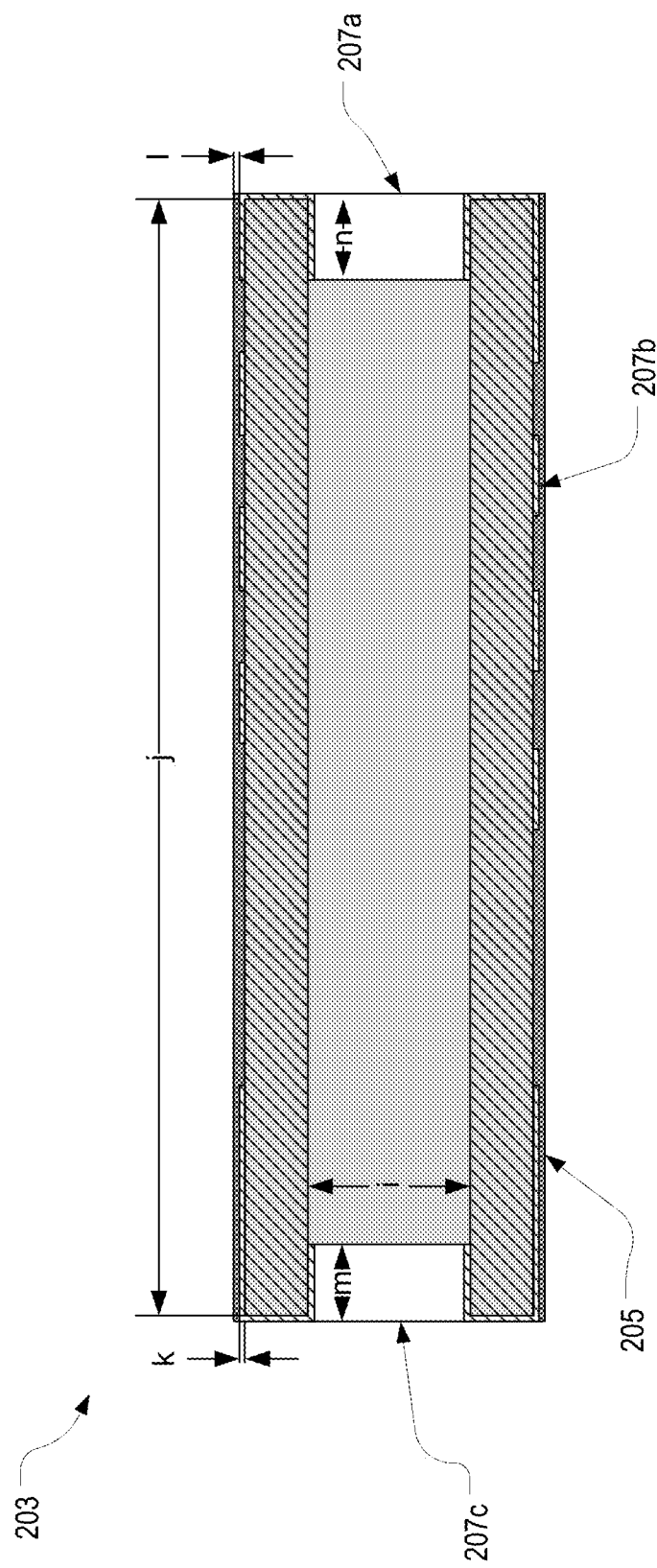
FIG. 5B illustrates a cross-sectional view of the distal shaft depicted in FIG. 5A with various dimensions labeled.

FIGS. 5A and 5B illustrate various dimensions of distal shaft 203 including of distal ring 207a, trace 207b, proximal ring 207c, and outer coating(s) 205. The specific dimensions may vary based on the intended use of emitter assembly 200. For example, the dimensions may vary based on the frequency (or wavelength) of the microwave energy employed as will be apparent to one of skill in the art.

The following dimensions are exemplary dimensions for an embodiment of emitter assembly 200 that is tuned for use at 915 MHz. These exemplary dimensions should not be construed as limiting the invention to an emitter assembly tuned to any particular frequency. Other dimensions could be employed and can be based on various factors including the frequency or frequencies at which the particular emitter assembly will be operated, the power at which the emitter assembly will be operated, the intended ablation pattern, etc.

With reference to FIG. 5A, the diameter of distal shaft 203 (dimension g) in this embodiment is 0.083 inches. However, a suitable diameter may also be within a range from 0.02 to 0.25 inches. The width of distal ring 207a and trace 207b and the spacing between portions of trace 207b (dimensions d, e, and f) is approximately 0.04 inches. However, a suitable width may also be within a range from 0.001 to 0.2 inches. The width of proximal ring 207c (dimension a) as well as the spacing between proximal ring 207c and trace 207b (dimension b) can be the same and in this embodiment is 0.1 inches. However, a suitable width and spacing may also be within a range from 0.001 to approximately 0.5 inches. The length of distal shaft 203 along which trace 207b extends (dimension c) is between 0.01 and 4.0 inches. The total length of trace 207b (i.e. the length passing around distal shaft 203) is between 0.1 and 9.0 inches. The total number of revolutions of trace 207b is approximately between 0.5 and 50.

With reference to FIG. 5B, the length of distal shaft 203 (dimension j) is approximately 0.45 inches. However, a suitable length may also be within a range from 0.02 to 4.0 inches. The internal diameter of distal shaft 203 (dimension i) is approximately 0.043 inches. However, a suitable internal diameter may also be within a range from 0.005 to 0.25 inches. The thickness of distal ring 207a, trace 207b, and proximal ring 207c (dimension k) is approximately 0.001 inches. However, a suitable thickness may also be within a range from 0.0001 to 0.004 inches. The depth of outer coating(s) 205 (dimension l) is approximately between 0.0001 and 0.003 inches. The width of proximal ring 207c and distal ring 207a within distal shaft 203 (dimensions m and n respectively) is approximately 0.04 inches. However, a suitable width may also be within a range from 0.005 to 0.25 inches. Although not shown, the thickness of first inner coating 401 can be between 0.0001 and 0.002 inches while the thickness of second inner coating 402 can be between 0.00005 and 0.001 inches when such coatings are employed. Also, conductor 206 can be configured with an outer diameter of approximately 0.047 inches. However, suitable outer diameters may also be within a range from 0.002 to 0.125 inches.

Variations in the above dimensions can also be employed even when configuring emitter assembly 200 for operation at 915 MHz. For example, optimal performance at 915 MHz may be obtained when dimensions e and f are set to different values (e.g. between 0.001 and 0.2 inches) or when the dimensions remain equal or substantially similar. In some embodiments, a different pattern for trace 207b can be employed other than the helical pattern depicted in the figures as long as dimensions e and f remain consistent with respect to one another. In other embodiment, dimensions e and f may not remain consistent. Suitable patterns include a back-and-forth spiraling pattern (as opposed to the depicted wrap-around helical pattern) or a stepped-up helical pattern (as opposed to the depicted gradually increasing or decreasing helical pattern).

In some embodiments, trace 207b may have a variable pattern. For example, the pitch of a helical or other pattern may vary. Varying the pitch can change the field intensity of the microwaves emitted from the trace. A smaller pitch will cause the windings of a helical trace to be spaced more closely and will therefore increase the field intensity along the portion of the emitter assembly with the smaller pitched trace. Traces that are more closely spaced will also create a greater density of heat. Accordingly, the pitch of a trace may be reduced nearer the proximal end of distal shaft 203 so that the heat density is greatest nearer proximal shaft 201. This can facilitate the transfer of heat to proximal shaft 201. In some embodiments, proximal and distal portions of trace 207b may have a smaller pitch than a middle portion of the trace such that the trace is more closely spaced in the proximal and distal portions than in the middle portion. Varying the pitch in this manner may create a spherical radiation pattern or potentially another desired non-spherical radiation pattern.

The width of trace 207b may also be varied. A thicker trace will allow more current flow. Accordingly, in some embodiments, a distal portion of the trace 207b may be thicker than a proximal portion to account for higher currents that pass through the distal portion.

Figure 6:
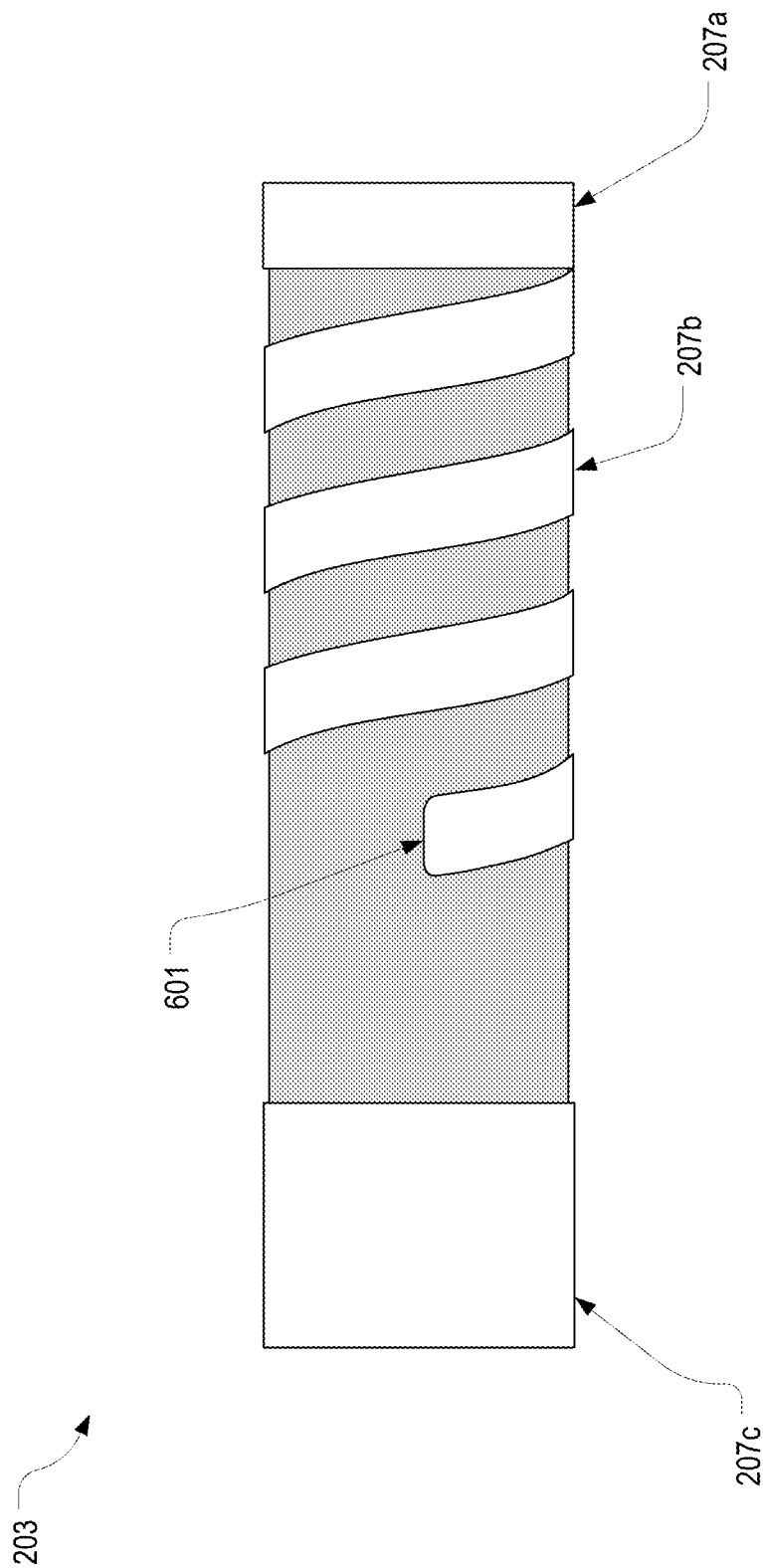
FIG. 6 illustrates a front view of an alternate embodiment of the distal shaft shown in FIG. 5A in which an end of the conductive trace is rounded.

FIG. 6 illustrates a variation of distal shaft 203 shown in FIG. 5A. As shown in FIG. 6, the proximal end 601 of trace 207b can be rounded. However, the proximal end 601 of trace 207b may also be square as depicted in the other figures, or may be another suitable shape.

Figure 7:
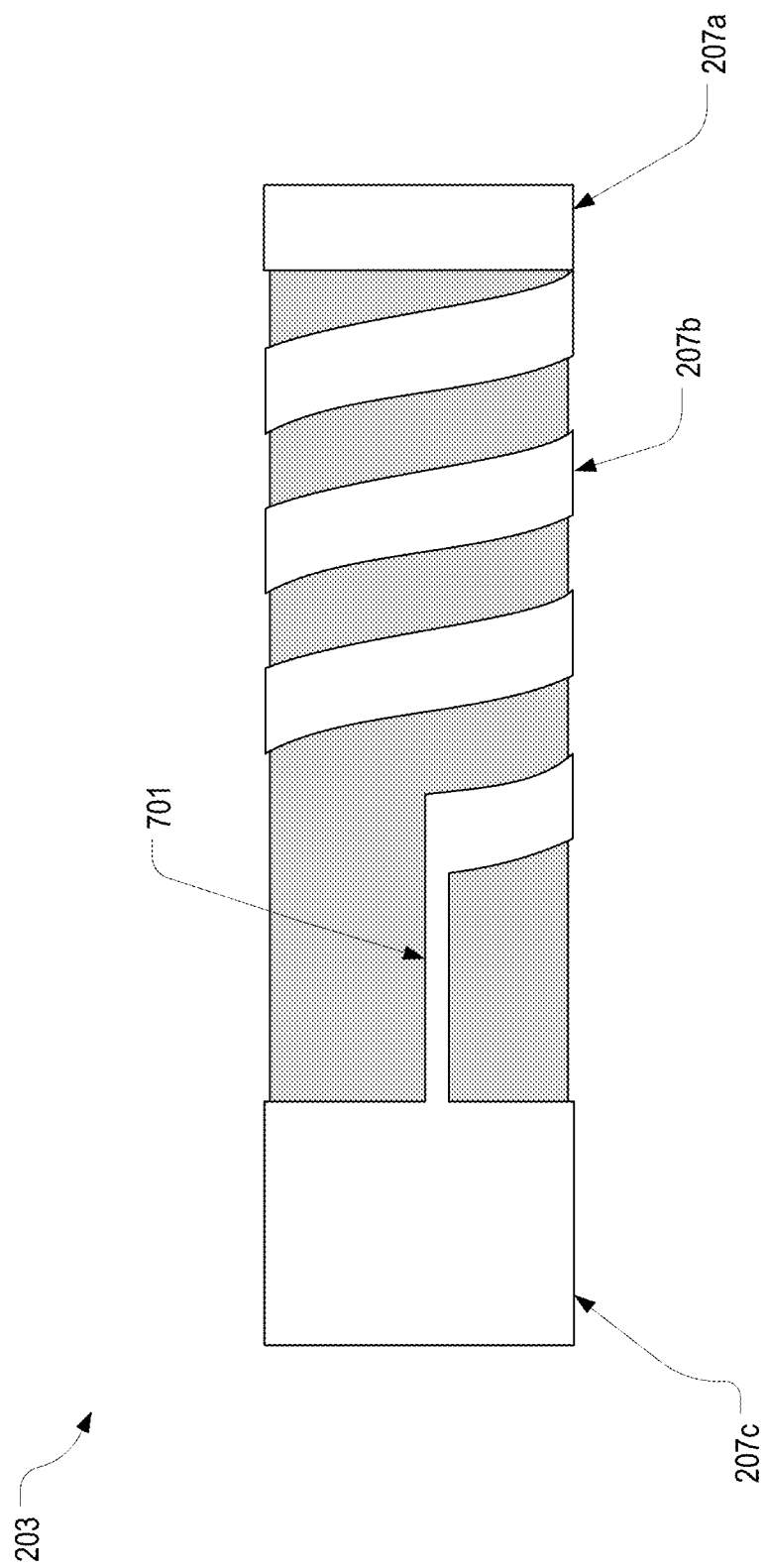
FIG. 7 illustrates a front view of another alternate embodiment of the distal shaft shown in FIG. 5A in which the conductive trace is connected to the proximal ring.

FIG. 7 illustrates another variation of distal shaft 203 shown in FIG. 5A. As shown in FIG. 7, trace 207b can include an extension 701 that connects trace 207b to proximal ring 207c. In a typical implementation where trace 207b receives microwave energy and proximal ring 207c is connected to ground, extension 701 can function to close the circuit. Using extension 701 in this manner can enable an emitter assembly (e.g. emitter assembly 200) to produce more heat over a time period and transmit higher powers. For example, by closing the circuit, extension 701 can make trace 207b (which functions as an antenna) less susceptible to changes in the surrounding tissue (e.g. changes in conductance, dielectric constant, etc.) that occur during an ablation procedure. Although extension 701 is shown as extending from the proximal most portion of trace 207b, it may also be positioned to extend from other locations along trace 207b. Extension 701 can also have other shapes in addition to the straight line shape shown in FIG. 7. In short, any extension that connects trace 207b and proximal ring 207c can be employed.

Figure 8:
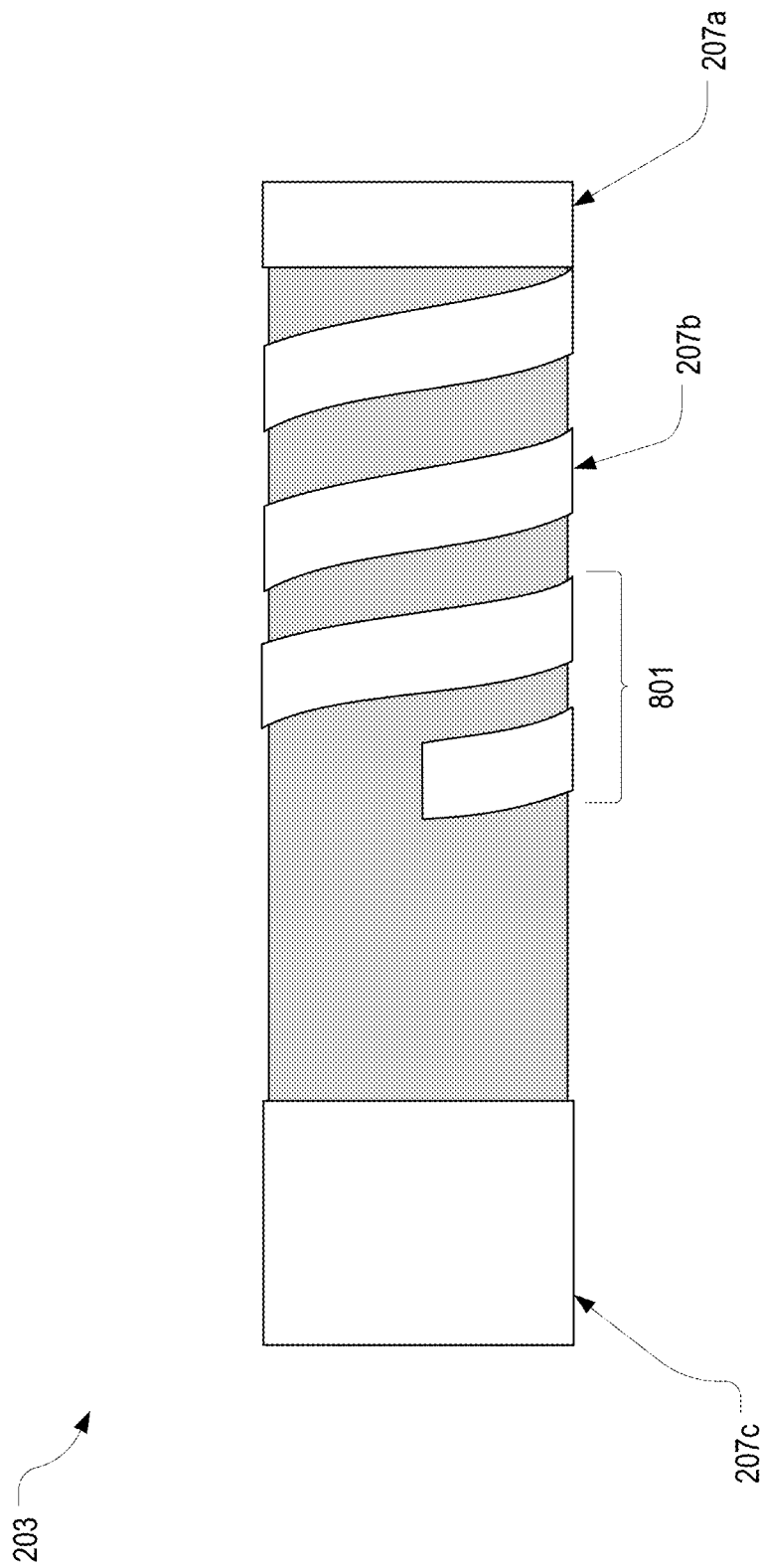
FIG. 8 illustrates a front view of another alternate embodiment of the distal shaft shown in FIG. 5A in which the pitch of the conductive trace is varied.

FIG. 8 illustrates another variation of distal shaft 203 shown in FIG. 5A. As shown in FIG. 8, trace 207b can have a varied pitch with portion 801 of trace 207b having a smaller pitch than the more distal portions.

Figure 9:
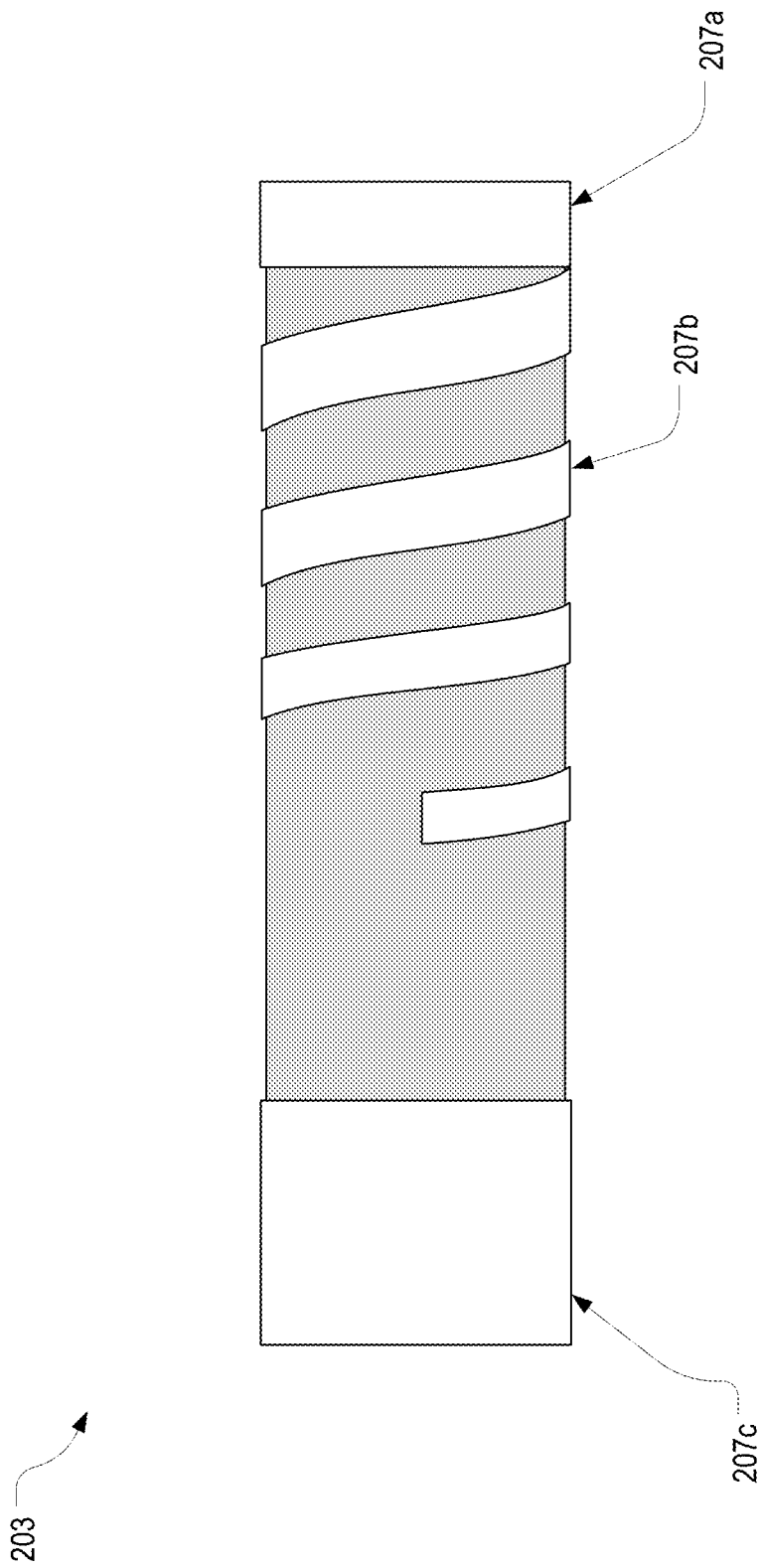
FIG. 9 illustrates a front view of another alternate embodiment of the distal shaft shown in FIG. 5A in which the width of the conductive trace is varied.

FIG. 9 illustrates another variation of distal shaft 203 shown in FIG. 5A. As shown in FIG. 9, trace 207b can have a varied width with a distal portion of trace 207b being thicker than a proximal portion.

Figure 10:
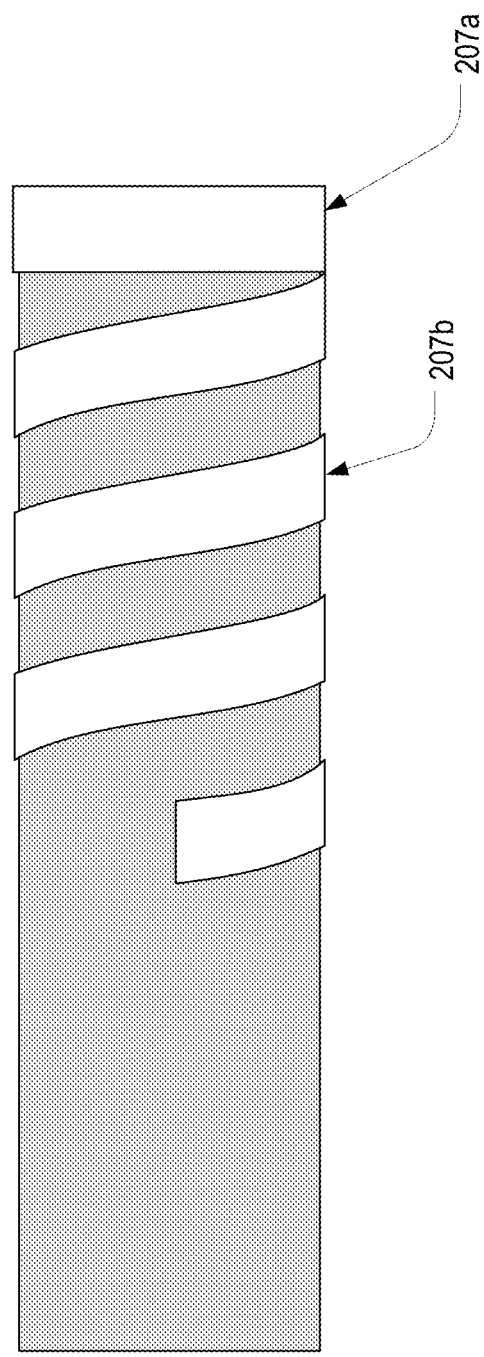
FIG. 10 illustrates a front view of another alternate embodiment of the distal shaft shown in FIG. 5A in which the distal shaft does not include a proximal ring.

FIG. 10 illustrates another variation of distal shaft 203 shown in FIG. 5A. As shown in FIG. 10, distal shaft 203 does not include a proximal ring.

Figure 11:
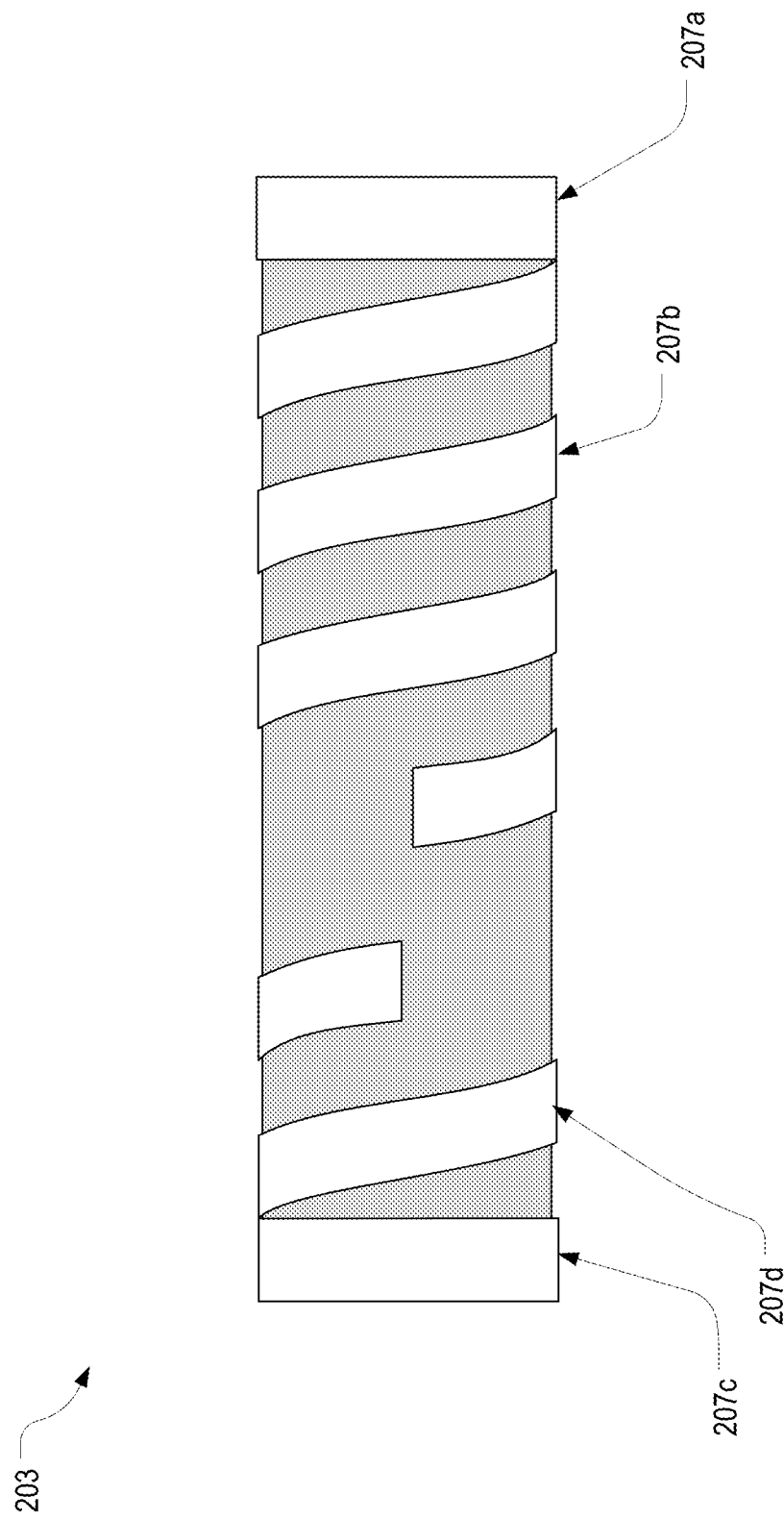
FIG. 11 illustrates a front view of an alternate embodiment of the distal shaft shown in FIG. 5A in which the distal shaft includes a second conductive trace.

FIG. 11 illustrates another variation of distal shaft 203 shown in FIG. 5A. As shown in FIG. 11, proximal ring 207c comprises a distally extending trace 207d. In some embodiments, such as shown in FIG. 11, a gap may exist between trace 207b and trace 207d. Alternatively, trace 207d may extend up to and even connect with trace 207b. Trace 207d can have any suitable pattern including any of the variations as described above for trace 207b.

Figure 12:
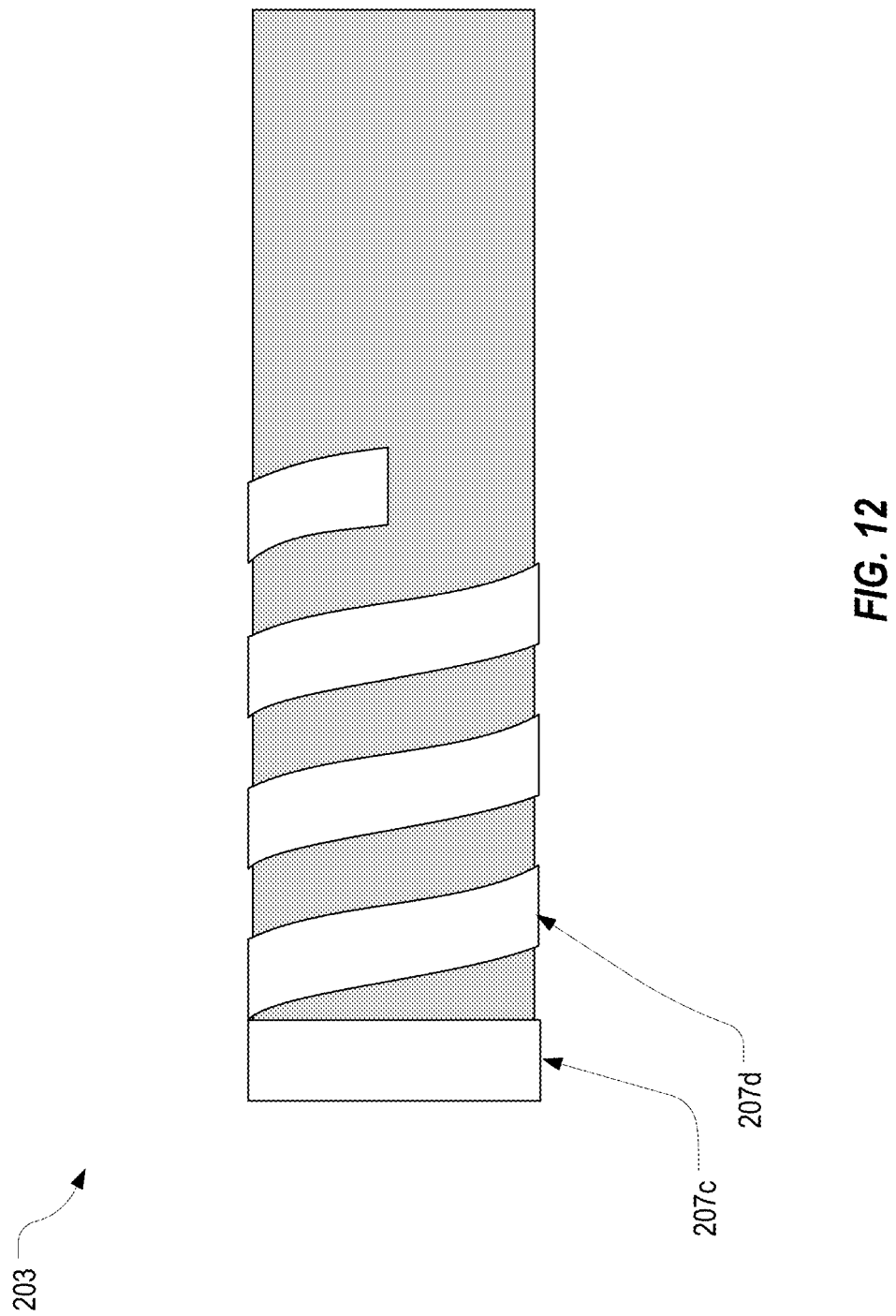
FIG. 12 illustrates a front view of an alternate embodiment of the distal shaft shown in FIG. 5A in which the distal shaft does not include a distal ring.

FIG. 12 illustrates another variation of distal shaft 203 shown in FIG. 5A. As shown in FIG. 12, distal shaft 203 does not include a distal ring, but includes a proximal ring 207c and a distally extending trace 207d. In such embodiments, trace 207d could be electrically connected to inner conductor 206a (e.g. via proximal ring 207c) to thereby function as an antenna.

Figure 13:
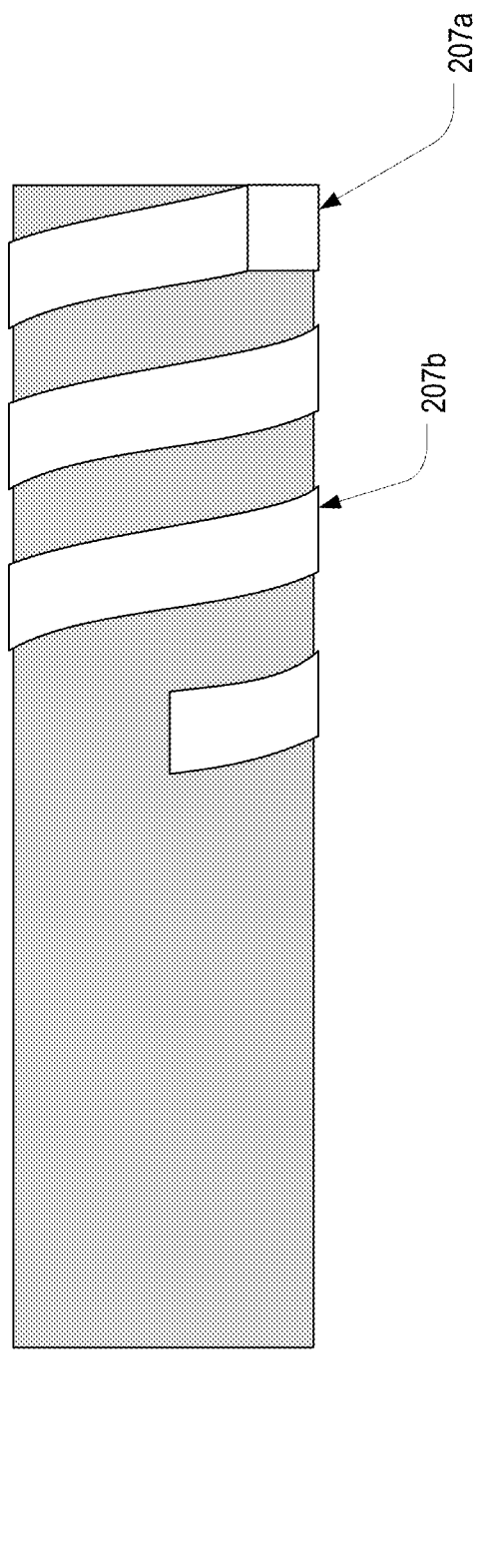
FIG. 13 illustrates a front view of an alternate embodiment of the distal shaft shown in FIG. 5A in which the distal shaft includes a distal ring that partially extends around the distal shaft.

FIG. 13 illustrates another variation of the distal shaft shown in FIG. 5A. As shown in FIG. 13, distal shaft 203 includes a distal ring 207a that extends only partially around distal shaft 203. Trace 207b connects with and extends from distal ring 207a. Distal ring 207a may extend around a similar portion or a different portion of the inner surface of distal shaft 203 or may extend completely around the inner surface.

Figure 14:
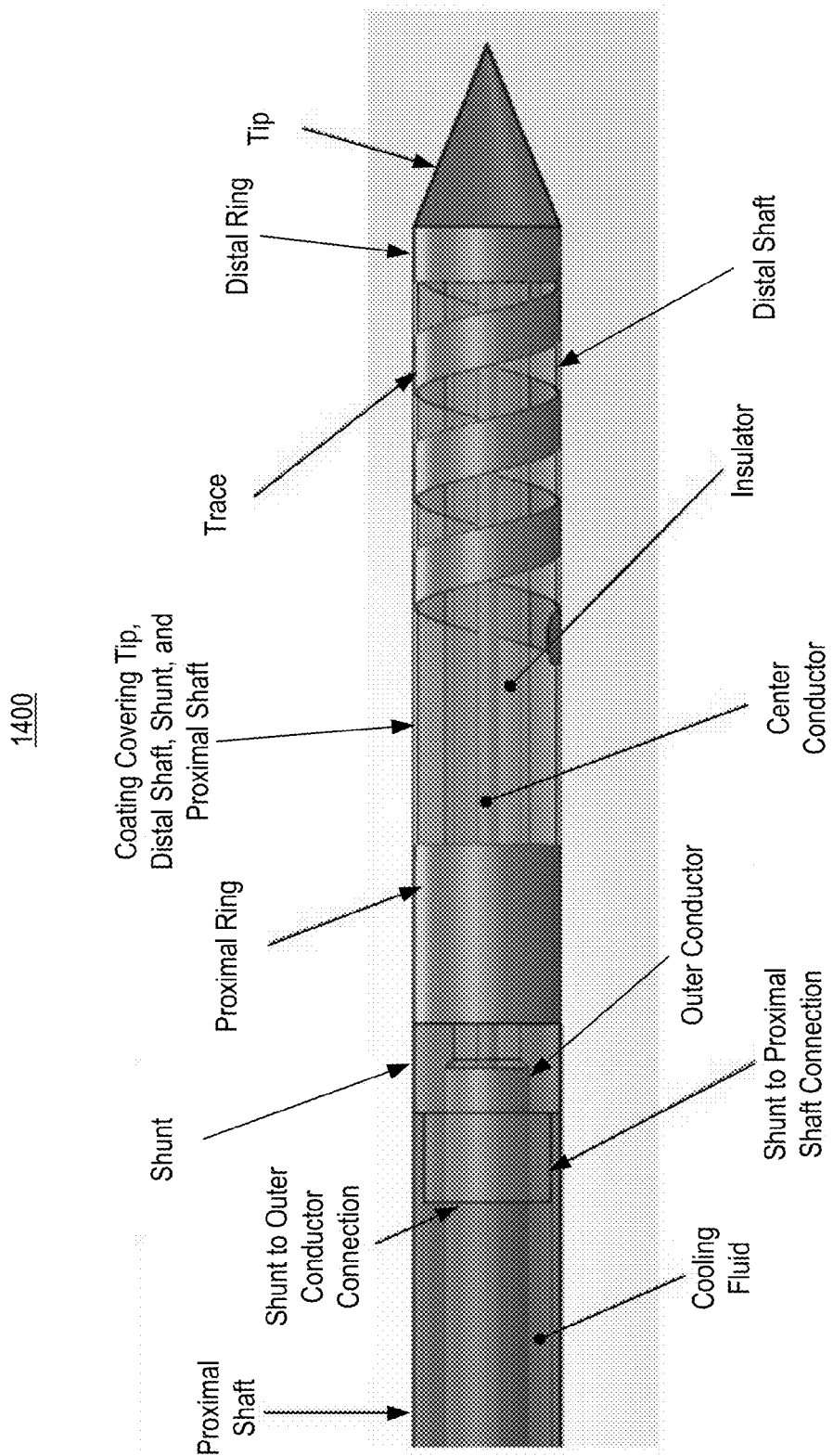
FIG. 14 illustrates a partially transparent front view of an example emitter assembly configured in accordance with one or more embodiments of the invention.

FIG. 14 illustrates another example emitter assembly 1400 that is configured in accordance with the above description. Emitter assembly 1400 includes a trace that extends around the distal shaft 3.5 times in a helical pattern. An outer dielectric coating (e.g. glass) covers the entire emitter assembly (i.e. the tip, distal shaft, shunt, and proximal shaft). A shunt extends into both the proximal shaft and the distal shaft and functions to form an electrical connection between the outer conductor and the proximal ring, and to form a thermal connection between the tip and the cooling fluid contained within the proximal shaft.

The present invention encompasses additional variations to the design described above. In some embodiments, an emitter assembly may not include shunt 202. For example, proximal shaft 201 and distal shaft 203 may be configured to directly couple together such as by brazing a joint between the two components or configuring an end of one component to insert within the end of the other component. In such cases, if a proximal ring 207c is included, distal shaft 203 can be configured to form an electrical connection between proximal ring 207c and outer conductor 206c (assuming distal ring 207a and trace 207b are used to form an antenna) or between proximal ring 207c and inner conductor 206a (assuming proximal ring 207c will function as the antenna).

In some embodiments, distal shaft 203 can be configured to form tip 204 rather than have a separate component for tip 204. In such cases, distal shaft 203 and tip 204 can comprise a single component formed of ceramic. In such embodiments, a distal ring 207a and trace 207b may not be included. Instead, proximal ring 207c may comprise a distally extending trace (e.g., similar to trace 207d) which is connected to inner conductor 206a. Alternatively, a distal ring 207a and trace 207b could be formed with distal shaft 203 including an opening or other electrically conductive channel for connecting inner conductor 206a with distal ring 207a.

In some embodiment, tip 204 can be formed of a non-conductive material. In such embodiments, distal ring 207a can extend onto an inner surface of distal shaft 203 to which inner conductor 206a can connect. Similarly, shunt 202 could be formed of a non-conductive material with proximal ring 207c extending onto an inner surface of distal shaft 203 for connecting outer conductor 206c (or, in some cases, inner conductor 206a) to proximal ring 207c.

In some embodiments, tip 204 can be comprised of two components. An inner component may be formed of a conductive material (e.g., a metal) which interconnects inner conductor 206a with distal ring 207a. An outer component may function as an end cap that is placed overtop the inner component. The outer component, in some embodiments, may be comprised of ceramic.

FIGS. 15A-15C illustrate different views of a tip 1500 that can be used in place of distal shaft 203 and tip 204. Tip 1500 comprises a non-conductive material such as ceramic. A proximal end of tip 1500 can be configured to insert into proximal shaft 201 when shunt 202 is not employed or to connect to proximal shaft 201 via shunt 202. A distally extending trace 1501 is formed on the outer surface of tip 1500. Trace 1501 includes an extension 1501a that extends onto an inner surface of tip 1500. When tip 1500 is connected to proximal shaft 201, whether directly or via shunt 202, inner conductor 206a can be connected to extension 1501a thereby supplying microwave energy to trace 1501. Tip 1500 can also include a metalized portion 1502 or forming an electrical connection with outer conductor 206c.

In other embodiments, tip 1500 may be used in conjunction with distal shaft 203. In such embodiments, portion 1502 can be electrically connected via outer conductor 206c to distal ring 207a thereby allowing trace 207b to form a ground plane. In some embodiments, an insulative coating (not shown) can be applied on tip 1500 prior to forming trace 1501. One or more outer coatings (e.g., similar to outer coating(s) 205) may also be applied after trace 1501 is formed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An emitter assembly for performing an ablation comprising:
   a proximal shaft;
   a distal shaft having an exterior surface;
   a tip that extends from a distal end of the distal shaft;
   an inner conductor that extends through the proximal shaft;
   an outer conductor; and
   a conductive trace metalized to the exterior surface of the distal shaft.

2. The emitter assembly of claim 1, wherein the distal shaft is comprised primarily of ceramic.

3. The emitter assembly of claim 2, wherein the ceramic comprises one of or both alumina based ceramics and zirconia based ceramics.

4. The emitter assembly of claim 1, wherein the tip is a separate component from the distal shaft.

5. The emitter assembly of claim 1, wherein the conductive trace spirals around the exterior surface.

6. The emitter assembly of claim 1, wherein a conductive distal ring is formed on one or both of an interior surface or an exterior surface of the distal shaft.

7. The emitter assembly of claim 6, wherein the tip forms an electrical connection between the inner conductor and the distal ring.

8. The emitter assembly of claim 6, wherein the conductive trace is electrically connected to the distal ring.

9. The emitter assembly of claim 1, wherein a conductive proximal ring is formed on one or both of an interior or an exterior surface of the distal shaft.

10. The emitter assembly of claim 9, wherein the conductive trace is electrically connected to the proximal ring.

11. The emitter assembly of claim 1, wherein the conductive trace extends in a proximal direction, and wherein a second conductive trace is formed on the exterior surface of the distal shaft that extends in a distal direction.

12. The emitter assembly of claim 1, further comprising: a shunt that connects the proximal shaft to the distal shaft.

13. The emitter assembly of claim 12, wherein the shunt forms an electrical connection with the outer conductor.

14. The emitter assembly of claim 13, wherein a conductive proximal ring is formed on one or both of an interior or an exterior surface of the distal shaft, the proximal ring being electrically connected to the shunt.

15. The emitter assembly of claim 12, wherein the distal shaft includes one or both of a conductive proximal ring and a conductive distal ring, and wherein the conductive trace extends from one or both of the proximal ring and distal ring.

16. The emitter assembly of claim 1, wherein the conductive trace extends in one of a proximal direction or a distal direction.

17. The emitter assembly of claim 1, further comprising: an insulator positioned between the inner and outer conductors, the insulator comprising PTFE or ceramic.

18. The emitter assembly of claim 1, further comprising: an outer coating comprising one or more layers, the outer coating covering at least a portion of an exterior surface of the distal shaft.

19. The emitter assembly of claim 18, wherein the outer coating covers one or more of the tip, a shunt that connects the proximal shaft to the distal shaft, or the proximal shaft.

20. The emitter assembly of claim 18, wherein the outer coating comprises at least one of glass, PTFE, or diamond-like carbon.

21. The emitter assembly of claim 1, further comprising: one or more inner coatings applied on an inner surface of the distal shaft.

22. The emitter assembly of claim 21, wherein one or both of a conductive proximal ring and a conductive distal ring are formed on an exterior surface of the distal shaft, and wherein the one or more inner coatings are applied overtop a portion of one or both of the proximal ring and distal ring that extends along the inner surface.

23. The emitter assembly of claim 1, wherein the tip is comprised of an inner and an outer component.

* * * * *